(12) United States Patent
Aarestad et al.

(10) Patent No.: US 11,123,218 B2
(45) Date of Patent: Sep. 21, 2021

(54) DEVICE AND METHOD FOR OPENING AN AIRWAY

(71) Applicant: SOMMETRICS, INC., Vista, CA (US)

(72) Inventors: Jerome K. Aarestad, Escondido, CA (US); Kent Gandola, San Diego, CA (US); David Giuntoli, San Diego, CA (US); Jeff Mullally, La Mesa, CA (US)

(73) Assignee: SOMMETRICS, INC., Vista, CA (US)

( * ) Notice: Subject to any disclaimer, the term of this patent is extended or adjusted under 35 U.S.C. 154(b) by 254 days.

(21) Appl. No.: 16/083,445

(22) PCT Filed: Mar. 8, 2017

(86) PCT No.: PCT/US2017/021450
§ 371 (c)(1),
(2) Date: Sep. 7, 2018

(87) PCT Pub. No.: WO2017/156190
PCT Pub. Date: Sep. 14, 2017

(65) Prior Publication Data
US 2019/0125572 A1    May 2, 2019

Related U.S. Application Data

(60) Provisional application No. 62/305,494, filed on Mar. 8, 2016.

(51) Int. Cl.
*A61F 5/56* (2006.01)
*A61H 9/00* (2006.01)
(Continued)

(52) U.S. Cl.
CPC .......... *A61F 5/56* (2013.01); *A61F 13/00068* (2013.01); *A61F 13/0216* (2013.01);
(Continued)

(58) Field of Classification Search
CPC .. A61F 5/56; A61F 13/00068; A61F 13/0216; A61F 5/3707; A61H 9/00;
(Continued)

(56) References Cited

U.S. PATENT DOCUMENTS

| | | |
|---|---|---|
| 4,257,407 A | 3/1981 | Macchi |
| 5,343,878 A | 9/1994 | Scarberry et al. |

(Continued)

OTHER PUBLICATIONS

International Search Report and Written Opinion issued in PCT/US2017/021450 dated May 31, 2017 (10 pages).

(Continued)

*Primary Examiner* — Tu A Vo
*Assistant Examiner* — Alexander Morales
(74) *Attorney, Agent, or Firm* — Acuity Law Group, PC; Michael A. Whittaker

(57) ABSTRACT

The present invention provides devices and methods for creating and/or maintaining patency of the upper airway passage. The device is configured to fit under the chin of a subject at an external location corresponding approximately with the subject's internal soft tissue associated with the neck's anterior triangle. The device includes structural elements designed to optimize comfort, compliance and seal achieved through minimizing the pressure variation along the contact surface of the therapy device.

17 Claims, 12 Drawing Sheets

(51) Int. Cl.
  *A61M 1/00* (2006.01)
  *A61F 13/02* (2006.01)
  *A61F 13/00* (2006.01)

(52) U.S. Cl.
  CPC ......... *A61H 9/0057* (2013.01); *A61M 1/0088* (2013.01); *A61H 2009/0064* (2013.01); *A61H 2201/1604* (2013.01); *A61H 2201/165* (2013.01); *A61H 2201/169* (2013.01); *A61H 2201/1609* (2013.01); *A61H 2205/022* (2013.01); *A61H 2205/026* (2013.01); *A61H 2205/04* (2013.01); *A61M 2210/065* (2013.01); *A61M 2210/0606* (2013.01)

(58) Field of Classification Search
  CPC ................. A61H 9/005; A61H 9/0057; A61H 9/0071–0092; A61H 2009/0064; A61H 2201/1604; A61H 2201/1609; A61H 2201/165; A61H 2201/169; A61H 2205/022; A61H 2205/026; A61H 2205/04; A61H 7/00; A61H 7/008; A61H 7/001; A61H 7/007; A61M 1/00; A61M 1/08; A61M 1/0088; A61M 1/009; A61M 16/00; A61M 16/04; A61M 16/0003; A61M 16/0009; A61M 16/0465; A61M 16/0468; A61M 16/0472; A61M 16/0497; A61M 16/0488; A61M 16/06; A61M 16/0688; A61M 16/0616; A61M 16/0627; A61M 2210/0606; A61M 2210/065; A61M 25/02; A61M 2025/028; A61M 39/0247; A61M 2039/0261; A61M 2039/0276; A61M 2039/0223

USPC ......................................................... 128/848
  See application file for complete search history.

(56) References Cited

U.S. PATENT DOCUMENTS

| | | | |
|---|---|---|---|
| 7,182,082 B2 | 2/2007 | Hoffrichter | |
| 7,762,263 B2 | 7/2010 | Aarestad et al. | |
| 7,762,263 C1 | 4/2013 | Aarestad et al. | |
| 9,820,881 B2 | 11/2017 | Aarestad et al. | |
| 2003/0167018 A1* | 9/2003 | Wyckoff | A61F 5/56 600/538 |
| 2006/0266369 A1 | 11/2006 | Atkinson et al. | |
| 2009/0177124 A1* | 7/2009 | Silwa | A61F 5/56 601/6 |
| 2010/0139667 A1 | 6/2010 | Atkinson et al. | |
| 2010/0275910 A1 | 11/2010 | Aarestad et al. | |
| 2010/0294284 A1 | 11/2010 | Hohenhorst et al. | |
| 2011/0066086 A1 | 3/2011 | Aarestad et al. | |
| 2012/0234330 A1* | 9/2012 | Saiz | A61F 5/055 128/848 |
| 2013/0274638 A1 | 10/2013 | Jennings et al. | |
| 2014/0144450 A1 | 5/2014 | Aarestad et al. | |
| 2015/0128956 A1* | 5/2015 | Matula, Jr. | A61F 5/042 128/845 |
| 2015/0173997 A1 | 6/2015 | Grashow | |
| 2016/0051391 A1* | 2/2016 | Abbott | A61H 7/001 602/18 |

OTHER PUBLICATIONS

The Extended European Search Report issued in EP 17764048 dated Feb. 27, 2020 (8 pages).

* cited by examiner

DEVICE AND METHOD FOR OPENING AN AIRWAY

The present invention is filed under 35 U.S.C. § 371 as the United States national phase of International Application No. PCT/US2017/021450, filed Mar. 8, 2017, which designated the United States and claims priority to U.S. Provisional Application No. 62/305,494, filed Mar. 8, 2016, which is hereby incorporated by reference including all tables, figures and claims.

BACKGROUND OF THE INVENTION

The following discussion of the background of the invention is merely provided to aid the reader in understanding the invention and is not admitted to describe or constitute prior art to the present invention.

The external application of negative pressure to patients for palliative or therapeutic purpose is well established in the medical arts.

U.S. Pat. Nos. 5,343,878, 7,182,082, and 7,762,263 describe various devices which purport to utilize external application of negative pressure upon the external neck surface of patients. A therapeutic appliance is typically provided that has a surface which is configured to enclose an external area of the throat (the term "throat" as used herein referring to the anterior portion of the neck extending approximately from the chin to the top of the sternum and laterally to a point posterior to the external jugular vein) overlying a portion of the upper respiratory passage. In certain embodiments, these appliances can provide a chamber (e.g., a hollow space filled with air molecules) lying between the interior surface of the chamber and the throat. The therapy appliance is operably connected to an air pump which is configured to produce a partial vacuum in this chamber. Application of a therapeutic level of negative pressure in the chamber elicits movement of the upper airway and may alleviate conditions such as snoring, sleep apnea, and full or partial airway collapse for example.

In these "negative pressure" therapeutic apparatuses and methods it is difficult to obtain a proper and comfortable fit between the apparatus and the patient to create and maintain the differential negative pressure (relative to atmospheric pressure for example) at the desired location on the patient. This is particularly true as the devices are intended for daily wear for many hours; thus, any points of high pressure from the device's sealing on the user's skin soon become too uncomfortable for continued use. Further, success of these negative pressure therapies is optimized by a device's ability to accommodate (flex, bend, flow, etc.) varying anatomical features (i.e. device compliance). User compliance with therapy is maximized by a good comfortable interface between the device and the user. Finally, the device should also accommodate movement to different sleeping positions without loss of seal.

BRIEF DESCRIPTION OF THE INVENTION

It is an object of the invention to provide a therapy device with sealed chamber and a seal adapted to form a conforming seal between a device that is intended to attach and seal to a patient's external tissue, such as a face, a neck, an area surrounding a wound, etc. This therapy device is particularly suited for forming a sealed chamber that is configured for the administration of negative pressure to a targeted therapy on the external tissue of an individual.

In a first aspect, the invention provides therapy devices configured for the administration of negative pressure upon the external surface of the individual. These therapy devices comprise:

a. a pressure containment chamber comprising
   (i) a flexible membrane which defines a chamber, an aperture through the flexible membrane, and
   (ii) a conforming sealing element adapted to form a seal when mated to the individual, wherein a first surface of the sealing element is configured to approximately conform to a continuous contact area on the individual defined by a first location corresponding to a first gonion on one side of the individual's mandibular body, a second location corresponding to the individual's mental protuberance, a third location corresponding to a second gonion on the opposite side of the individual's mandibular body, and a fourth location corresponding to the individual's thyroid cartilage, b. a skeleton structure that is formed as either a discrete element from the pressure containment structure, or as a unitary element of the pressure containment chamber. Whether as an integral or discrete skeleton structure, it is configured to be positioned inside the pressure containment structure and comprises
   (i) a structural member configured to mechanically support the aperture and comprising at least, first and second hinge points on a first side thereof and at least, third and fourth hinge points on a second side thereof, wherein the first and third hinge points are preferably configured to be positioned on opposite sides of the mental protuberance and the second and fourth hinge points are configured to be positioned on opposite sides of the thyroid cartilage when the chamber is mated to the individual,
   (ii) a strapping member that extends at least from the first hinge point to the third hinge point and is configured to contact the sealing element at a location within the chamber which corresponds to the second location,
   (iii) a first spar member, whether unitary or discrete relative to the flexible membrane, configured to mechanically support the chamber and comprising a plurality of arcuate spars, wherein each spar in the first spar member is configured to extend from a first end thereof that is located proximal to the structural member to a second end thereof that is located at the sealing element at the first location, wherein each of the spars in the first spar member are spaced apart laterally from one another, wherein each of the spars in the first spar member are affixed to a first lateral joining structure at the first end thereof and to a second lateral joining structure at the second end thereof, and wherein the first lateral joining structure is rotationally engaged with the structural member at the first and second hinge points thereof,
   (iv) a second spar member, whether unitary or discrete relative to the flexible membrane, configured to mechanically support the chamber and comprising a plurality of arcuate spars, wherein each spar in the second spar member is configured to extend from a first end thereof that is located proximal to the structural member to a second end thereof that is located at the sealing element at the third location, wherein each of the spars in the second spar member are spaced apart laterally from one another, wherein each of the spars in the second spar member are affixed to a third lateral joining structure at the first end thereof and to a fourth lateral joining structure at the second end thereof, and wherein the third lateral joining structure is rotationally engaged with the structural member at the third and fourth hinge points thereof, (v) a first plurality of arcuate ribs, whether unitary or discrete relative to the flexible membrane, running approximately perpendicular to the spars of the first spar member, wherein each rib in the first plurality of ribs are spaced apart laterally from one another and physically constrained to maintain an inter-rib spacing, wherein each rib in the first plurality of ribs is configured to extend from a first end thereof that is located at the sealing element as it extends from the first location to the second location to a second end thereof that is located at the sealing element as it extends from the first location to the fourth location, and (vi) a second plurality of arcuate ribs, whether unitary or discrete relative to the flexible membrane, running approximately perpendicular to the spars of the second spar member, wherein each rib in the second plurality of ribs are spaced apart laterally from one another and physically constrained to maintain an inter-rib spacing, wherein each rib in the second plurality of ribs is configured to extend from a first end thereof that is located at the sealing element as it extends from the third location to the second location to a second end thereof that is located at the sealing element as it extends from the second location to the fourth location; and (c) an air pump operably connected to the chamber at the aperture to produce the therapeutic level of negative pressure within the chamber.

In a related aspect, the invention provides therapy devices that comprise:

a. a pressure containment structure comprising
   (i) a flexible membrane which bounds a chamber,
   (ii) an aperture through the flexible membrane, and
   (iii) a flange element adapted to form a sealing surface when mated to the individual, wherein a first surface of the flange element is configured to approximately conform to a continuous contact area on the individual defined by a first location corresponding to a first gonion on one side of the individual's mandibular body, a second location corresponding to the individual's mental protuberance, a third location corresponding to a second gonion on the opposite side of the individual's mandibular body, and a fourth location corresponding to the individual's thyroid cartilage;

b. an curvilinear structure that is formed in a unitary manner with the pressure containment structure, the curvilinear structure comprising
   (i) a structural member configured to mechanically support the aperture and comprising first spar attachments locations on a first side thereof and second spar attachment locations on a second side thereof,
   (ii) a first plurality of spars configured to mechanically support the pressure containment structure, wherein each spar is unitary with the first spar attachment locations at a first end thereof and each spar extends at a second end thereof to the flange element at the first location, wherein each of the spars in the first plurality of spars are spaced apart laterally from one another,
   (iii) a second plurality of spars configured to mechanically support the pressure containment structure, wherein each spar is unitary with the second spar attachment locations at a first end thereof and each spar extends at a second end thereof to the flange element at the third location, wherein each of the spars in the second plurality of spars are spaced apart laterally from one another;
   (iv) a first plurality of arcuate ribs running approximately perpendicular to the spars of the first plurality of spars, wherein each rib in the first plurality of ribs are spaced apart laterally from one another and intersect with the first plurality of spars in a unitary manner, wherein each rib in the first plurality of ribs is configured to extend from a first end thereof that is located at the flange element as it extends from the first location to the second location to a second end thereof that is located at the flange element as it extends from the first location to the fourth location; and
   (v) a second plurality of arcuate ribs running approximately perpendicular to the spars of the second plurality of spars, wherein each rib in the second plurality of ribs are spaced apart laterally from one another and intersect with the second plurality of spars in a unitary manner, wherein each rib in the second plurality of ribs is configured to extend from a first end thereof that is located at the flange element as it extends from the third location to the second location to a second end thereof that is located at the flange element as it extends from the second location to the fourth location; and (c) an air pump operably connected to the chamber at the aperture to produce the therapeutic level of negative pressure within the chamber.

The term pressure containment structure, as used herein refers to the elements of the therapy device that contain the negative pressure during use. The pressure containment structure comprising a flexible membrane that defines a chamber element, one or more apertures in the flexible membrane through which a vacuum source (for example) may be affixed or applied through, a sealing element affixed to the flexible membrane that forms the sealing surface between the chamber element and the individual.

In certain embodiments, the pressure containment structure may be mechanically supported by a skeleton structure that may be formed as a discrete element containing a structural member with or without one or a plurality of arcuate ribs and spars.

In certain embodiments, the pressure containment structure may be mechanically supported by an endoskeleton or exoskeleton structure that may be formed as a discrete element containing a structural member with or without one or a plurality of arcuate ribs and spars.

In certain embodiments, the pressure containment structure may be, partially or in full, mechanically supported by curvilinear structural members molded into or molded with the flexible membrane that form a curvilinear structure wherein the curvilinear structural members can be interior to the pressure containment structure, exterior to the pressure containment structure, central to the pressure containment structure, all, in part or a combination thereof. Curvilinear structural members are defined as supporting elements that follow the curvature of the dome of the pressure containment structure. Curvilinear structural members can be intersecting, not intersecting or a combination thereof and in instances where curvilinear features intersect, points of intersection may contain features to impart rigidity, for example increased thickness to increase stiffness, or decreasing thickness to increase flexibility creating hinge-type property, for example.

In certain embodiments, the pressure containment structure and mechanical support structure elements whether discrete or integrated may be of the same or differing material.

In certain embodiments, structural elements and features thereof, of the therapy device can be adjusted to balance the distribution of loads when a therapeutic level of negative pressure is applied in the chamber so that the user experiences an approximately uniform contact pressure of the device when in use. These structural elements can include but are not limited to dome material, dome material thickness, flange material, flange thickness, flange width and supporting elements such as arcuate ribs, arcuate spars and or curvilinear structural members, whether discrete or unitary. Structural elements can be modified to accommodate an aperture whether located at a central or non-central location on the pressure containment structure. Structural elements can also be modified to accommodate instances where a plurality of apertures is present, whether apertures are located at a central, non-central, symmetric or non-symmetric location on the pressure containment structure to maintain the users' perception of an approximately uniform contact pressure of the device on the user when in use.

In embodiments where one or a plurality of arcuate ribs, arcuate spars, curvilinear structural members or a combination thereof are present, the spacing between the arcuate ribs, arcuate spars, curvilinear structural members or combination thereof, may vary to create sectional properties to impart desired mechanical function wherein sectional properties can be structural characteristics and or load distributing properties to resist collapse of the dome or maximize rebound following a collapse for example.

The therapy device is configured to provide an approximately constant and evenly distributed contact pressure across the entire contact area between the individual and the chamber when the therapy device is mated to the individual and a therapeutic level of negative pressure is applied within the chamber. This approximate contact pressure may range from 0.9 to 1.5 times, and preferably be about 1.1 to 1.3 times, the negative pressure within the therapy device. In certain embodiments, when the therapy device is mated to the individual and a therapeutic level of negative pressure is applied within the chamber, the approximate contact pressure applied to the skin surface is approximately 1.2 times the negative pressure within the chamber.

In related aspects, the present invention relates to methods of applying negative pressure therapy to an individual in need thereof, comprising mating a therapy device as described herein to the individual, and applying a therapeutic level of negative pressure within the chamber, thereby increasing patency of the airway of the individual. Such methods can be for treatment of sleep apnea; for treatment of snoring; for treatment of full or partial upper airway collapse; for treatment of full or partial upper airway obstruction; for negative pressure treatment of a wound caused by, for example an injury or a surgery; etc.

The terms "external area" and "external surface" of an individual as used herein refers to a portion of the external skin surface of the individual. In various embodiments, the therapy device is configured to provide optimized fitting parameters, for example, seal, comfort and local device compliance throughout all points of contact. This is preferably achieved by minimizing the contact pressure differential from one point of contact on the skin of a patient to another through design features of the cushion element and design features of the sealed chamber element of a negative pressure therapy device.

In certain embodiments, the structural elements of the therapy device including but not limited to the pressure containment structure, unitary and/or discrete skeleton structure including the location, width, spacing and of the arcuate ribs, arcuate spars, straps, hinge points and adjustable members varies around the circumferential dimension of the therapy device. By varying the structural elements and properties, the magnitude of forces applied to the skin surface of the individual can be varied from point to point around the continuous contact area. Further, by varying the structural elements and properties, the flexible membrane of a therapy device can allow for device compliance characteristics, for example, lateral sheer and can be supported with minimal dome collapse and maximum dome rebound following collapse, when a therapeutic level of negative pressure is applied. In this manner, the force applied to the external surface of the individual at any point along the circumferential dimension of the sealing element may be made to be "constant." In this context, the term "constant" as used herein, refers to maintaining the force within about 20%, and more preferably about 10%, of the average force along the entire circumferential dimension of the sealing element, where the force at each point along the circumferential dimension of the sealing element is measured at the location on the width dimension of the flange element at which sealing element contacts the user.

In certain embodiments, the skeleton structure contains an aperture supported by a structural member comprising hinge points on either side of the aperture wherein the hinge points allow movement of the spar members independent of the support structure wherein adjustable members contact the spar members creating a series of sequential stops to limit the rotation of the spar members through the hinge point(s).

In embodiments where the pressure containment structure is mechanically supported, partially or in full, by elements molded into or molded with the flexible membrane forming an integrated curvilinear structure an aperture may also be supported as an integrated element or discrete element wherein the aperture is approximately shaped to fit, receive and or secure a pump housing element for example.

It is preferred that the therapy device comprises an unloaded spacing measured between the first and third locations that is narrower than a spacing obtained when the device is mated to the individual and the therapeutic level of negative pressure is applied within the chamber. This unloaded spacing can impart a preload force to the individual by the chamber prior to the application of negative pressure. In preferred embodiments, the skeleton structure of the therapy device contains adjustable members that are configured to physically limit the rotation of the first and second spar members such that the spacing measure between the first and third locations can be further narrowed to obtain additional preload force.

In certain embodiments, the sealing element may comprise a tacky material inherent in, or positioned on, all or a portion of the contact area. By way of example only, the tacky material can comprise a room-temperature vulcanizing (RTV) silicone. The tacky material may be a single layer, or may be a component of a lamination stack of materials positioned on all or a portion of the contact area.

Any and all air pump types find use in the present invention, provided that a therapeutic level of vacuum can be achieved by the pump. In certain embodiments, the air pump may be connected to the apparatus via a hose or tube. Preferably, the air pump is wearable by the patient and is battery powered, and most preferably the air pump is configured integrally to the apparatus. In certain embodiments, the air pump may be a manual squeeze bulb, or may be electric and comprise a piezoelectric material configured to provide an oscillatory pumping motion. It is most preferred that the oscillatory pumping motion operates at a frequency greater than 500 Hz.

In those embodiments where the air pump is configured integrally to the apparatus, the flexible membrane element and the aperture of the pressure containment structure can comprise an opening into which the air pump engages, wherein when engaged, sealing features along the periphery and or face of the opening forms an airtight seal with the air pump. A compliant sealing ring may be provided within the opening into which the air pump engages. The compliant sealing ring may be provided integrally with the chamber element, and most preferably as a unitary structure with the chamber element. Alternatively, the compliant sealing ring and the chamber element are discrete structures, where the sealing ring may be in the form of a separate O-ring for example. As an alternative to providing the compliant sealing ring as a component of the chamber element, the compliant sealing ring may be provided as a component of the air pump. A locking ring may also be provided, located between the compliant sealing ring on the air pump and the flexible membrane of the therapy device on the outer surface of the flexible membrane of the pressure containment structure, to compress the flexible membrane in between the outer surface of the pressure containment structure and the aperture opening.

In certain embodiments, the chamber element comprises one or more apertures creating vent elements that provide an airflow into the chamber when the therapy device is mated to the individual and a therapeutic level of negative pressure is applied. The apertures, located distal to the intake of a pump element provide a flow of air through the chamber that may assist to decrease temperature and humidity within the interior of the chamber. The aperture(s) providing an airflow that is preferably between about 10 mL/min and about 300 mL/min, and most preferably between about 20 mL/min and about 150 mL/min, and still more preferably between about 40 mL/min and about 100 mL/min.

In some embodiments, the vent element can comprise an aperture and a filter element within the aperture, wherein the filter element comprises a pore size of about 1.0 μm or less, such as a pore size of about 0.7 μm. The filter element can be configured as a replaceable element and the size adjusted to provide an airflow preferably between about 10 mL/min and about 300 mL/min, and most preferably between about 20 mL/min and about 150 mL/min, and still more preferably between about 40 mL/min and about 100 mL/min.

In yet another embodiment, the vent element can comprise one or a plurality holes distal to the intake of the pump element and of a sufficiently small size to exclude debris from entering the chamber. The hole size further enables the desired airflow of preferably between about 10 mL/min and about 300 mL/min, and most preferably between about 20 mL/min and about 150 mL/min, and still more preferably between about 40 mL/min and about 100 mL/min, wherein the hole size is between about 25 um to about 200 um and more preferably an airflow of about 40 mL/min with a hole size between about 73 microns to about 77 microns.

Alternatively, the level of airflow can vary. In certain embodiments, the level of airflow tied to the therapeutic level of vacuum; that is, a higher level of vacuum can be accompanied by a higher level of airflow due to the differential in pressure between the atmospheric side of the vent elements and the interior of the chamber. In certain embodiments, the vacuum source may be used in a variable manner to maintain the therapeutic level of vacuum within a specified range rather than a single value, and the level of airflow can vary in concert with the level of vacuum.

In related aspects, the present invention relates to methods of applying negative pressure therapy to an individual in need thereof, comprising mating a therapy device as described herein to the individual, and applying a therapeutic level of negative pressure within the chamber, thereby increasing patency of the airway of the individual. Such methods can be for treatment of sleep apnea; for treatment of snoring; for treatment of full or partial upper airway collapse; for treatment of full or partial upper airway obstruction; for negative pressure treatment of a wound caused by, for example an injury or a surgery; etc.

DETAILED DESCRIPTION OF THE INVENTION

Figure 1:
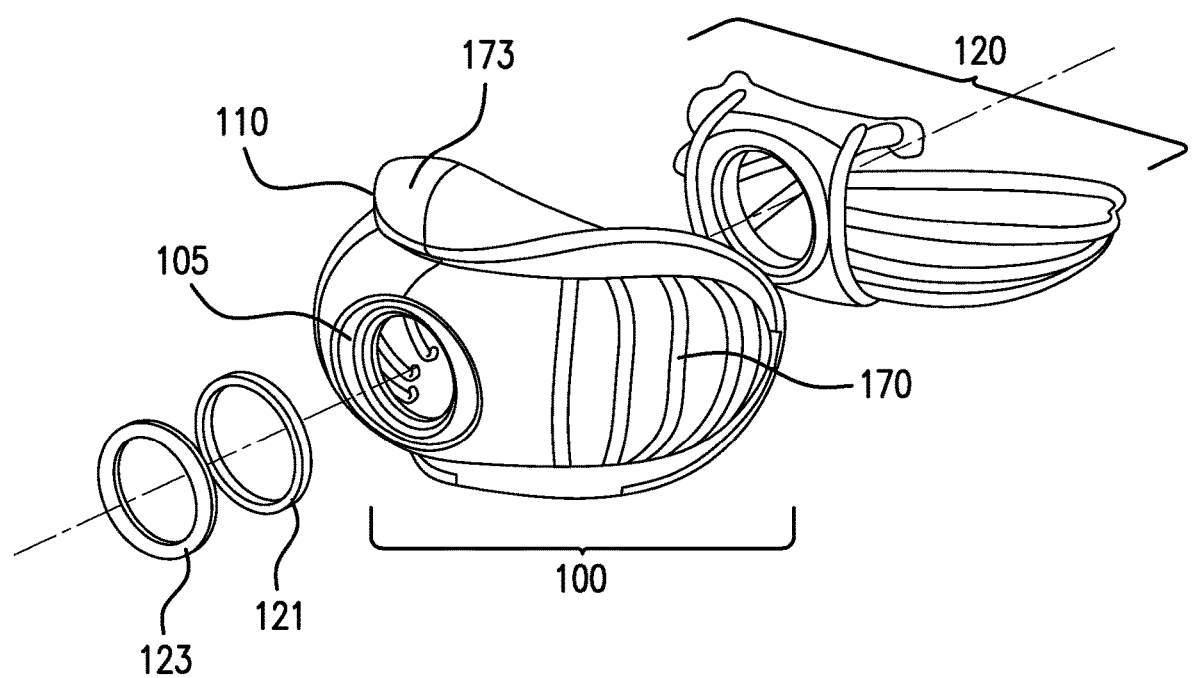
FIG. 1 is a view of an illustrative embodiment of the therapy device including the pressure containment structure 100, central aperture 105, sealing element 110, endoskeleton structure 120, compliant sealing ring element 121, spacer element 123, plurality of arcuate ribs 170 and chin cup element 173.
Figure 2:
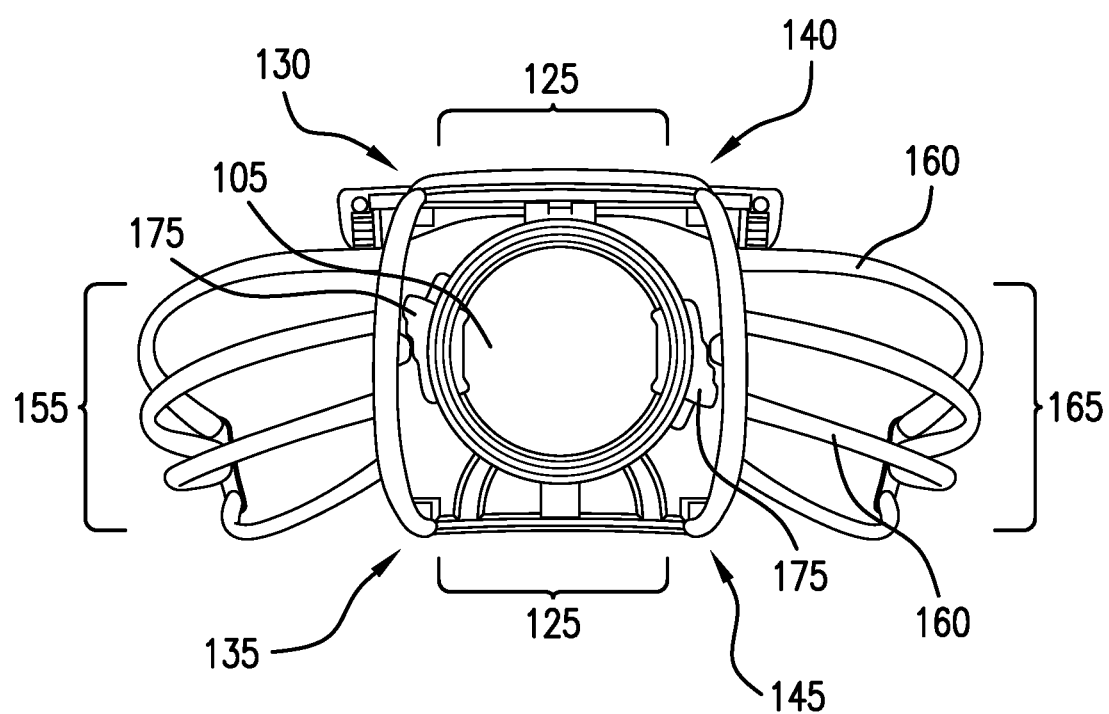
FIG. 2 is a front view of an illustrative embodiment of the endoskeleton structure 120, central aperture 105, central structural member 125, first hinge point, 130, second hinge point 135, third hinge point, 140, fourth hinge point 145, first spar member 155, arcuate spar(s) 160, second spar member 165 and adjustable member(s) 175.

The present invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the present invention. The examples used herein are intended merely to facilitate an understanding of ways in which the invention may be practiced and to further enable those of skill in the art to practice the invention. Accordingly, the examples should not be construed as limiting the scope of the invention. In the drawings, like reference numerals designate corresponding parts throughout the several views.

In the present invention, a therapy device is designed for a negative pressure therapy device that maximizes comfort and seal efficiency ultimately optimizing device efficacy and user compliance. The negative pressure therapy device is described below for use in the opening of the upper airway when placed upon the neck of a subject over a surface corresponding to approximately the upper airway of the subject. This exemplary application of the technology is not meant to be limiting. The therapy device comprised of a chamber and a sealing element configured to be the contacting surface between the chamber and the user described herein is configured to provide for regional load equalization over the interface between a negative pressure therapy device and the three dimensionally varying skin surface of the user so as to maintain a near uniform contact pressure over this non-uniform surface.

In particular, the therapy device referred to herein relates but is not limited to an external therapy appliance for relieving upper airway obstruction. U.S. patent application Ser. No. 12/002,515, 12/993,311 and 13/881,836 which are hereby incorporated by reference in their entirety including all tables, figures and claims, describes a therapy appliance for relieving airway obstruction. Increasing the patency of the upper airway of an individual alleviates conditions such a snoring, sleep apnea, full or partial upper airway collapse. As described therein, a device is configured to fit under the chin of a user at an external location corresponding to the soft tissues overlying the upper respiratory passages of the neck.

For purposes of the patent application, the term "about" refers to +/−10% of any given value.

The therapy device of the present invention comprises a flexible membrane element, one or more sealable apertures through the flexible membrane element and a compliant sealing element positioned along the edge or face of the flexible membrane element along the circumferential dimension of the sealing element to form an airtight junction between the sealing element and the flexible membrane element. The junction between the sealing element and the chamber element is referred to herein as the "root" of the junction. As used herein a compliant element is defined as a one that is flexible, for example the compliant sealing element, though in the approximate shape of the contact surface a target therapy area is flexible as to accommodate variation.

As used herein, the term "circumferential dimension" refers to a continuous location along the width of the sealing element, in some cases, for example where the chamber element makes continuous contact with the sealing element. As used herein, the "root" is the location at which the chamber element contacts the sealing element and is of a width enclosed by the thickness of the chamber element. The chamber element may be affixed to the sealing element as an integral structure, unitary structure or discrete structures. An "integral structure" refers to a structure that is a complete piece formed by joining two or more components which, once joined, become a single piece that is not separable without destroying the device. A "unitary structure" refers to a structure that is a singular structure formed or molded as a single piece. Two elements are "discrete structures" if the two (or more) structures form a single working structure, but retain individual characteristics and can be separated in the normal course of use of the single working structure and then reassembled.

Surface variation of the therapy site, both permanent and occasional (i.e., the shape of the mandible, transition points from neck to mandible, tissue types, scars, facial hair and/or skin blemishes differential forces applied to different portions of the seal caused by movement of the wearer, etc.) can undesirably disrupt the seal between the negative pressure therapy device and user. The present invention provides devices, systems and methods of use that can accommodate varying facial contours/features and adapt to movement, resulting in greater comfort, reduced vacuum leakage and improved therapeutic efficacy.

The flexible membrane element and the sealing element of the sealing surface incorporate cantilever-like structures, hoop load-like structures and or a combination of the two, adapted to have sectional properties that allow for stiffness, flexibility and uniform regional compliance and/or force load on the skin surface of the individual. As used herein, "regional compliance" refers to a property of the device that permits the device to "mold" itself to a surface and or surface variation on the contact surface with the wearer. As described hereinafter, uniform regional compliance is provided, in part, by the sectional properties or structural features associated with a region on the chamber element, sealing element or both.

The sealing element may be in the form of a flange comprising a flexible, elastic material that can be uniform in thickness and width but also vary in thickness and width to achieve the structural properties desired at locations along the contact surface of the therapy device. Further, the location of the chamber element at the root location of the flange of the sealing element may be varied to adjust and equalize the contact pressure of the therapy device when a therapeutic level of negative pressure is applied. U.S. Provisional Patent Application No.: 62/281,063 filed: Jan. 20, 2016, titled: "Device and Method for Opening an Airway," and incorporated herein by reference, discusses variation of flange and chamber characteristics for the balancing of contact pressure In certain embodiments, the sealing element may be a cushion element containing a series of layers, including an air layer and a foam layer housed in a fluidly sealed chamber, to provide for a cushioning surface. The inner surface of the flange being that which makes contact with the flexible membrane element and the outer surface of the cushion element being that which makes contact with the skin of the user. U.S. Provisional Patent Application No.: 62/260,211 filed, Nov. 25, 2015 titled: "Chamber Cushion, Seal and Use Thereof", incorporated herein by reference discusses such a cushioned sealing element.

The cushion element of the sealing surface is adapted to have sectional properties that allow for flexibility and uniform regional compliance. As used herein, "uniform regional compliance" refers to a property of the cushion element that permits the cushion element to "mold" itself to a surface and or surface variation on the contact surface with the wearer. As described hereinafter, this uniform regional compliance is provided, in part, by the sectional properties or features associated with a region on the cushion element.

The cushion element comprises a fluidly sealed chamber; and a foam layer and/or a semi-rigid ribbon layer housed within the fluidly sealed chamber. The term "fluidly sealed" refers to a chamber that retains the fluid contained within the chamber for a period of time required for normal use of the chamber. By way of example, a latex balloon is "fluidly sealed" to helium if normal use of the balloon is for 6 hours, despite the fact that over time that helium may ultimately leak from the balloon, and despite the fact that the balloon may burst if put under abnormal conditions.

Optionally, an adhesive layer is located on the surface of the sealing element that makes contact with the user. This aims to reduce movement of the device on the wearer as well as enhance the seal and cushioning on the wearer. These elements are configured to maintain an approximate uniform contact pressure with minimized pressure variations along the skin of an individual through all points of contact of the therapy device on a patient. By "minimized pressure variation" means a pressure at any point between the contact surface of the sealing element and the patient's tissue varies by no more than about 20%, and preferably no more than about 10% or about 5%, from the average pressure across the entire contact surface. The outer contact surface, as used herein, is the surface of the sealing element of the therapy device that makes contact with the skin of the individual forming the contact and sealing surface of the therapy device.

In certain embodiments, the sealing element of the invention provides a contact interface of a negative pressure therapy device configured to conform to a continuous contact area on the individual at the external area of the neck approximately corresponding to the anterior triangle of the neck. The term "approximately corresponding to" an anatomical location refers to contacting closely to the actual location, shape or size but perhaps not necessarily completely, accurately or exactly.

Figure 6A:
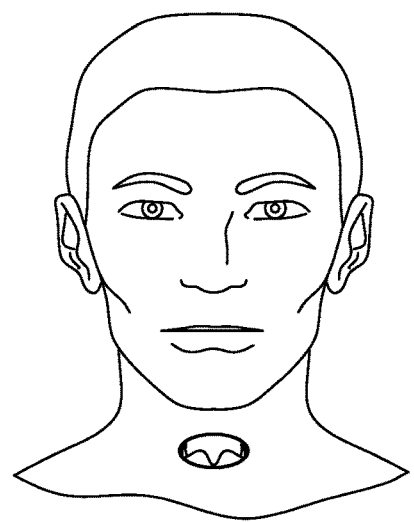
FIG. 6A depicts a region approximately corresponding to the thyroid cartilage bounded by the dotted lines.
Figure 6B:
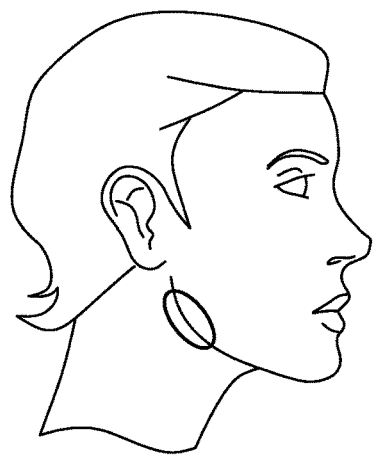
FIG. 6B depicts a region approximately corresponding to gonion bounded by the dotted lines.
Figure 6C:
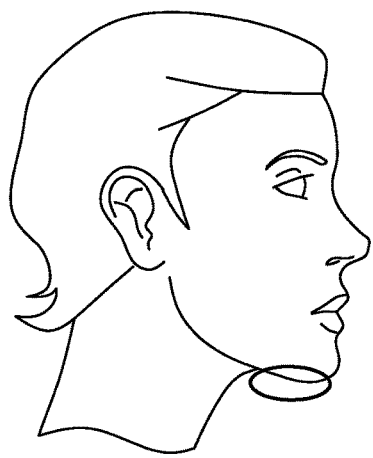
FIG. 6C depicts a region approximately corresponding to the mental protuberance bounded by the dotted lines.

Most preferably, the sealing element is configured to follow the contour of the therapy device which is designed to approximately conform to an individual from approximately a first location corresponding to a first gonion on one side of the individuals mandibular body to a second location corresponding to the individuals mental protuberance to a third location corresponding to the second gonion on the opposite side of the individual's mandibular body and a fourth location corresponding to the individuals thyroid cartilage further configured to return to approximately the first location corresponding to the first gonion The gonion, as used herein, describes the approximate location on each side of the lower jaw on an individual at the mandibular angle. The mandibular protuberance, as used herein, describes the approximate location of the chin, the center of which may be depressed but raised on either side forming the mental tubercles. The thyroid cartilage, as used herein, describes the approximate location of the large cartilage of the larynx in humans. A region approximately corresponding to the thyroid cartilage is depicted by the dotted lines in FIG. 6A; a region approximately corresponding to the gonion is depicted by the dotted lines in FIG. 6B; and a region approximately corresponding to the mental protuberance is depicted by the dotted lines in FIG. 6C. Note that FIGS. 6B and C show a right profile, and a similar region is present on the left profile.

In certain embodiments, the flexible membrane of the pressure containment structure of the present invention is a chamber, approximately a dome, oval in appearance, with a curvature from the middle of the dome that creates a collar to cover an area over the upper airway of an individual. The flexible membrane, containing an aperture through which an air pump may be affixed to and or through. The flexible membrane further being made of one or more layers wherein a plurality of accurate ribs that run approximately vertically for example from the interior of the sealing element at the second location on the individual to the interior of the sealing element at the fourth location of the individual and perpendicular to spars that may run lengthwise from the first and second location on an individual. As used herein arcuate indicates that the feature (the ribs) have a curved shape. The ribs are spaced apart laterally from one another and are physically constrained to maintain the inter-rib spacing. The ribs may be constrained for example between one or more layers of the flexible membrane during a forming process, affixed to the flexible membrane, inserted into sleeves in the flexible membrane or molded as a unitary element of the flexible membrane. The ribs contain a first curved surface that is configured to form a parallel curve to the inner surface of the chamber and to face toward the outer aspect of the flexible membrane. A parallel curve is similar to parallel line and can be defined as a curve that mirrors a given curve at an offset. The parallel curve provides for a point of contact that is normal such that when a downward force is applied, for example when a therapeutic level of negative pressure is applied, a shear force resists lateral movement and further provides for a transfer of force in a downward direction.

In embodiments, the flexible membrane of the pressure containment structure of the present invention is a chamber, approximately a dome, oval in appearance, with a curvature from the middle of the dome that creates a collar to cover an area over the upper airway of an individual. The flexible membrane containing one or a plurality of apertures through which an air pump may be affixed to and or through. The flexible membrane being made with one or a plurality of vertical curvilinear structural members, horizontal curvilinear structural members, forming a curvilinear support structural, that is molded as a unitary element of the flexible membrane. As used herein, curvilinear indicates the unitary structural member have a curved shape that follows the curvature of the dome of the pressure containment structure. The curvilinear structural members(s) may be biased toward the exterior of the chambers flexible membrane, central to the chamber flexible membrane, interior to the flexible membrane or a varying combination thereof. In further embodiments, the curvilinear structural members can be angled, vertical, horizontal or a combination of one or more these orientations through the pressure containment structure so as to provide regional support via a unitary curvilinear support structure. As used herein, angled is defined as not vertical or horizontal.

In preferred embodiments, the negative pressure therapy device contains structural elements adapted to guide correct placement and orientation of the device on the user, for example a chin cup element 173. As used herein a "chin cup" refers to a discrete feature on the negative pressure therapy device which provides a recess configured to receive the chin of the wearer when the negative pressure therapy device is properly mated to the wearer. During application of the negative pressure therapy device, the chin cup provides a consistent point of reference on which the negative pressure therapy device can mate with the wearer. The shape of the chin cup may vary to allow for anatomical variation in patients. For example, the chin cup may be somewhat deeper for use in a subject having mandibular prognathia; somewhat shallower for use in a subject having mandibular retrognathia; or somewhat larger in volume for a subject having macrogenia. Further, the chin cup may or may not be included as part of the sealing surface of the sealing element.

In various embodiments, the present invention comprises a symmetric vacuum chamber with a flat contact surface adapted to fit to a flat uniform surface and to provide minimized pressure variation throughout all points of contact when a vacuum is applied. In other various embodiments, the present invention comprises a vacuum chamber with a contact surface configured to adapt to the inherent anatomical variations of an individual's face. The curved, "wraparound" shape that the negative pressure therapy device must assume can cause the "station load" through different contact points to vary in the absence of the design features described herein. For example, absent a feature or features designed to accommodate for station load variation, at points furthest from the center of the dome of the therapy device, toward the narrow end portions of the oval, the station load decreases due to a lesser vacuum cross section over the contact point(s). As used herein, "station load" is the force or pressure which is applied at a discrete area of contact of the device (a "station") on the skin of an individual when the device is mated to the individual and a therapeutic level of negative pressure is applied.

In certain embodiments, the present invention comprises an endoskeleton structure that is formed as either a discrete and/or integrated element from the pressure containment structure. As used herein, an endoskeleton structure is defined as an internal frame positioned within the flexible membrane element configured to mechanically support features of the pressure containment system. As used herein, mechanically support is defined as holding up or bearing all or part of the pressure containment structure.

In certain embodiments, the present invention comprises an exoskeletal structure that is formed as either a discrete and/or integrated element from the pressure containment structure. As used herein, an exoskeleton structure is defined as an external frame or support structure positioned on the exterior of the flexible membrane element, configured to mechanically support features of the pressure containment system.

In certain embodiments, the present invention comprises curvilinear structural supporting elements molded interior to, exterior to, within, or a combination thereof the pressure containment structure creating a unitary element. As used herein, elements molded with the pressure containment structure can be of the same, similar or differing materials and can be also be affixed to create the unitary structure. Similar materials, as used herein, is defined as substantially the same material with differing properties, for example, differing durometers. Further, the present invention may also comprise a combination of supporting elements, for example both unitary and discrete structures.

The endoskeleton structure contains a central structure member configured to mechanically support the central aperture and central aperture of the flexible membrane and first and second spar members located on either side of the central structure member configured to mechanically support the flexible membrane of the chamber and distribute load outwardly toward the first and third locations of the therapy device.

The first and second spar members each contain a plurality of arcuate spars that extend from a first and third location proximal to and on either side of the central structural member, to a second and fourth location respectively that is located at the sealing element on the interior of the pressure containment structure at locations corresponding to the first and third locations of the individual. As used herein arcuate indicates that the feature has a curved shape. The arcuate spars are affixed to lateral structures at a first and third lateral joining structure(s) located proximal to the central structural member and a second and fourth lateral joining structure respectively located proximal to the first and third locations of the individual respectively. Lateral joining structures as used herein are defined as approximately perpendicular structural elements that form the joining surfaces of the arcuate spars. The arcuate spars and lateral joining surfaces form the spar members.

The spars in the first and second spar members comprise a curved surface that is configured to face outward toward and laying in contact with the inner surface the flexible membrane element of the chamber. The curved surfaces are configured to form a parallel curve to the inner surface of the chamber such that when a therapeutic level of negative pressure is applied a normal (downward) force is generated on the curved surface of the spar members that resists shear/lateral movement of the first and second spar members relative to the inner surface of the flexible membrane. Further, the first and second spar members are configured to distribute load outwardly from the central structural member to the sealing element making contact with the first and third locations on the user when a therapeutic level of negative pressure is applied.

In certain embodiments, the first and second spar members are affixed to the central structural member however in preferred embodiments the first and second spar members and the central aperture contain hinge points that rotationally engage the spar members to the central structural member. The central structural member may have one or more hinge points on opposite sides of the central structural member that engages with one or more hinge points on the first and third lateral joining surfaces of the first and second spar members. Any suitable hinge mechanism may be used for example a living hinge which is a thin piece of flexible material made from same material as the pieces it connects, or a pivoting joint which is a joint that only allows rotation about one or more axis.

The endoskeleton structure further contains a strapping member on the central structural member at location corresponding to approximately the second location on the individual. The strapping member extends from points on the central structural member near the first and third hinge points and acts to provide additional mechanical support to the therapy device at the second location on the individual when a therapeutic level of negative pressure is applied.

In certain embodiments of the present invention the pressure containment structure and supporting elements are of a unitary structure for example, features for the purpose of supporting the flexible membrane are formed as integrated elements to the pressure containment structure. As used herein, unitary structure is defined as an integral molded or formed element as part of the flexible membrane element configured to mechanically support features of the pressure containment system. Integrated elements may be located interior to, exterior to central to or a combination thereof to the flexible membrane.

In embodiments of the invention, integrated elements forming a unitary structure may have features that provide sectional properties and/or directional properties. As used herein, sectional properties are defined as discrete regions that have mechanical function, for example but not limited to support of a flexible membrane at a desired location and or at all locations. As used herein, directional properties are defined as the ability of integrated elements or features of the like to transmit or direct force from one point to another, for example from a central location of the dome to a peripheral location of the dome. Features of integrated elements may include but are not limited to, thickness, tapering, shape and direction of molded elements or a combination thereof.

In certain embodiments of the present invention the pressure containment structure may contain supporting elements that are of unitary structure and of discrete structure. For example, the pressure containment structure may contain a discrete central structural member that is configured to mechanically support one or a plurality of apertures in the flexible membrane and portions of the flexible membrane proximal to the apertures using one or a plurality of spar like supporting features located on either side of the central structure member. Further, areas of the flexible membrane not supported by the discrete central structural member may contain unitary elements molded into the flexible membrane configured to mechanically support the flexible membrane of the chamber and distribute load outwardly toward the first and third locations of the therapy device.

Structural elements that are unitary to the pressure containment structure may be of the same material and can achieve strength by being thicker than the flexible membrane. Structural elements that are unitary to the pressure containment structure may be of similar material whereby the material is the same but a mechanical property of the material differs, for example, durometer. A support structure containing curvilinear supporting members made of a higher durometer material than that of the flexible membrane can allow for the features to be thinner than if the features are made of the same durometer of the flexible membrane.

In certain embodiments, the present invention comprises a chamber having a shape that when unloaded, i.e. not on the patient, has spacing between the first and third locations that is narrower than the spacing that is obtained when the chamber is mated to the individual and a therapeutic level of negative pressure is applied. The narrower spacing of the unloaded device creates a preload force that is applied to the individual by the chamber prior to the application of negative pressure. In further embodiments, the present invention comprises adjustable members located on the central support structure between the support structure and the spar members that can further narrow the spacing of the unloaded device. The adjustable member containing a series of surfaces sequentially increasing in height such that when a higher surface is selected the distance between the spar member and the central support structure increases resulting in a narrowing of the space corresponding to the first and third locations on the individual.

As discussed herein, the sealing element of the instant invention forms the interface between the chamber element of the therapy device and the contact surface of the individual. The flexible membrane chamber element of the instant invention forms the dome/chamber of the therapy device. These elements comprise structural features that provide minimized pressure variation at stations where contact pressure variation can occur as a result of either anatomical variation, tissue variation, inherent therapy device design, and or movement during usage. The sealing element and flexible membrane chamber element thereby providing features to the therapy device to minimize peak contact pressure values, minimize the variance from station to station, and equalize the contact pressure of the therapy device when a therapeutic level of negative pressure is applied to provide an effective seal.

The term "seal" as used in this context is not to necessarily imply that a perfect seal is formed between the therapy device and the contact surface of the individual. Rather, a "seal" is a portion of the device which mates to the wearer and maintains a therapeutic level of vacuum. A certain amount of leakage at the seal may be tolerated so long as the desired negative pressure can be achieved and maintained. Preferred operational vacuum levels are in a range of between about 7.6 hPa to about 61 hPa. Preferred forces applied to the user's neck tissues in order to assist in opening the upper airway passages are in a range of about 0.5 kilogram to about 6.68 kilograms. The term "about" and "approximately" as used herein with regard to any value refers to +/−10% of that value.

The dome/chamber enclosed by the chamber provides a finite volume which must be evacuated to deliver the desired partial vacuum level. Once generated, the partial vacuum will decay at a rate which is primarily controlled by leakage of air into the chamber past the flange seal, one or more pump seals and other venting features integrated into the dome not including features integrated into the dome. In certain embodiments, the chamber encloses a volume of between approximately 8 mL and about 200 mL. Preferably, the leakage is no more than between about 0 mL/min and about 8.0 mL/min, and most preferably no more than about 1.6 mL/min.

The therapy device may comprise one or more vent elements. As used herein a vent element is an aperture through the therapy device that provides airflow in to the chamber when the chamber is mated to the individual and a therapeutic level of negative pressure is applied within the chamber. The aperture(s) can be in any suitable location on the device however in some embodiments the aperture(s) may be located at the top of the chamber, where they are less susceptible to occlusion resulting from debris and or tissue ingress into the chamber and closer to locations one and three on the individual where they induce airflow more globally throughout the interior of the chamber. The vent element(s) may simply be an aperture such that when the chamber is mated to the individual and a therapeutic level of negative pressure is applied, an airflow between about 30 mL/min and about 100 mL/min is achieved or an aperture through which a filter element can be inserted to create filtered airflow such that when the chamber is mated to the individual and a therapeutic level of negative pressure is applied an airflow between about 30 mL/min and about 100 mL/min is achieved. The filter element can be a replaceable element and comprise a pore size of between about 0.25 µm and about 1.0 µm or less such that when the chamber is mated to the individual and a therapeutic level of negative pressure is applied, an airflow between about 30 mL/min and about 100 mL/min is achieved. In certain embodiments, the airflow is between about 30 mL/min and about 50 mL/min.

The present invention provides both sufficient regional, and overall, compliance of the therapy device such that local bottoming/regional collapse of the device does not occur under load. As used herein, "regional compliance" of the device refers to the ability of individual stations of the device to accommodate a therapeutic level of vacuum without complete compression at that station. As used herein, "overall compliance" of the device refers to the ability of the device to accommodate a therapeutic level of vacuum without complete compression of the device. Further, bottoming or "regional collapse", as used herein, is defined as a complete or near complete compression of the device that its resistance to further compression is no longer possible. This results in a hardening of supporting structure(s) by the flexible portions of the device under a heavy load, and loss of comfort by the wearer.

The sealing element and chamber element are designed to create uniform contact pressure onto the skin of the user when a therapeutic level of negative pressure is applied. The sealing element is preferably a perpendicular width (wide and narrow) and thickness to achieve the desired contact pressure properties. The perpendicular width component is the total width of the sealing, from the tip of the outside edge of the sealing element through the root and to the tip of the inside edge of the sealing element. The width of sealing element may vary along the peripheral axis of the contact area of the sealing element to accommodate for station load variations due to non-uniform shape of the therapy device that contains a chamber that is oval in shape and further contains a central bend to accommodate the mating surface on the neck of the patient corresponding to approximately the upper airway and maintain a constant contact pressure of the negative pressure therapy device.

In various embodiments of the sealing element, locations on the flange element of the device may be substantially wider than other locations. In one aspect, the total flange width may vary from approximately 28.0 millimeters to approximately 17.0 millimeters, (FIG. 9). "Substantially wider" as used herein refers to an increase in width of at least about 10%, more preferably at least about 20%, and still more preferably at least about 30% or more from one location to another, for example in an embodiment of the invention the width of the flange element at the fourth location corresponding to approximately the middle of the neck of the user is approximately 39% wider than the first and third locations that corresponding to the mandible and gonion regions of the user. Wider sections may be found in regions where a larger load displacement is needed for example at the second and fourth locations and narrower sections may be found in regions where smaller load displacement is needed for example at the first and third locations on the user.

The thickness of the flange element may also vary along the perpendicular width along the circumference of contact surface of the therapy device to accommodate for anatomical variation and varying vacuum cross section. As used herein, thick or thin, describes the distance between the surface of the flange contacting the individual and the (distal) surface of the flange element contacting the chamber element of the vacuum chamber of a negative pressure therapy device. The thickness of the flange element at the root may vary from approximately 4.5 millimeters to 1.0 millimeters at the inside of the root and 3.0 millimeters to 1.2 millimeters at the outside of the root. For example, the thickness of the flange element at the junction at the first and third locations on the user may be about 1.6 millimeters inside the root and 2.10 millimeters outside the root.

In certain aspects, locations on the flange element of the device may vary in thickness such that some portions are substantially thicker than others. For example, locations of the flange element may vary in thickness such that on location is substantially thicker than another. As used herein, "substantially thicker" refers to an increase in thickness of at least about 20%, more preferably at least about 30%, and still more preferably at least about 50% or more. For example, in an embodiment of the invention the thickness at approximately the second location is approximately 64% thicker that the first and third locations and the first and third locations are approximately 30% thicker than the fourth location.

The thickness of the flange element may further taper outwardly from the root location to a final flange thickness of approximately 0.7 millimeters to approximately 0.1 millimeters. The taper may begin at the root continuing to the inside or outside edge of the flange or the taper may also begin at points about 10%, 15%, 20%, 25%, 30%, 35%, 40%, 45%, 50%, 55%, 60%, 65%, 70%, 75%, 80%, 85%, 90% or 95% away from the tip of the flange element and continue to the inside or outside edge of the flange element to a desired final thickness of approximately 0.7-0.1 millimeters. The taper of the flange at its inner and outer edges assisting in the elimination of edge effects, allowing for minimized tissue irritation and damage. As used herein, "edge effects" refer to the irritation, (redness, swelling) of tissue caused by prolonged contact pressure of a sharp edge on the skin. The tapering of edges provides for a more flexible and softer edge of the flange The chamber element is stiff along its length and the flange will not appreciably deflect longitudinally. Therefore, in addressing the dynamic shape of the target therapy area, regions of the therapy device contain accommodating design features, for example, the variations in the width and thickness of the flange element, that are designed to minimize high pressure points and eliminate contact pressure variations of the therapy device along its contact surface when placed on the user and a therapeutic level of negative pressure is applied.

In regions where the flange contacts a substantially flat surface of the user, the chamber element and flange element can act as an "I-beam" where the force exhibited by the flange on the user is a more linear downward force and cantilever-like. The flange element inside and outside the root point of the chamber element flex according to the thickness of material with the tapered ends of the flange element flexing the most creating a soft transition on the skin of the user eliminating edge effects as above. As used herein cantilever-like forces are a measurement of the downward force of the chamber divided by the area of the flange at a given point. By way of example, in regions where the flange element lays flat across the skin, cantilever forces can be balanced by altering the width and thickness of the flange, for example where there is a high vacuum cross section and where larger load distribution is desired (ie. lower contact pressure), a flange with a larger perpendicular width may be utilized and similarly in regions where a smaller load distribution is desired (ie higher contact pressure) a flange with a smaller perpendicular width may be utilized The thickness dimensions of the flange element can give the flange element properties such that in portions of the device, if the flange element is too thin, though it may be very flexible it will have little to no load distributing properties, can bottom out creating point(s) of high contact pressure from the root of the chamber element resulting in leaks and/or discomfort. If the flange element is too thick it will affect its ability to change direction for example be unable to conform to the acute change from the surface of the neck over the mandible toward the ear for example and further allow for an undesirable level of sheer or lateral movement. In a similar fashion, if the width of the flange element is too small it can create a point(s) of high pressure and too wide it may create unnecessary bulk affecting fit and effective therapy area. Transition in widths taper gradually and the aspect ratio minimizes positional instability and optimizes flexibility.

In regions where the flange contacts a curved surface of the user, for example around the chin and over the mandible, the forces observed contain an additional hoop-like force component as the flange bends around those features. "Hoop-like forces" as used herein describe the distribution of force exerted circumferentially, for example, as the flange element travels around location four of the user, the curvature adds additional stiffness to the flange inside and outside the root of the chamber element. In these regions where the added force component of hoop loads exists, the thickness of the flange element may be decreased and the perpendicular width of the flange element may be increased to effectively distribute the load of the chamber and minimize contact pressure variation from station to station when a therapeutic level of negative pressure is applied.

The term "contact pressure" as used herein refers to a pressure imparted on the surface of the skin by the contact surface of the device. Its value can depend on the vacuum present as well as the structural characteristics of the flange such as the perpendicular width and surface area of the contact surface, and can vary at different locations on the flange.

A larger "perpendicular width" of a contact surface (meaning the direction that is perpendicular to the longest axis of the contact surface, which longest axis may be curved) will have a lower overall contact pressure under the same vacuum pressure as a contact surface with a smaller perpendicular width due to the increased surface area at that particular station of the contact surface. Therefore, in regions where the dome station pressure load is low, the contact surface of the flange can be designed to be of a smaller perpendicular width to effectively increase and "balance" the contact pressure and in regions where the dome station pressure is high, the contact surface of the flange can be designed to be of a larger perpendicular width to effectively decrease and balance the contact pressure where the dome station load is high.

In certain embodiments, the location of the chamber element on the flange element (the root location) may vary from the mid-point, inward or outward to further aid in equalizing the contact pressure of the therapy device on the user when a therapeutic level of negative pressure is applied creating and maintaining the balance point of the flange element on the user. For example, movement of the root of the edge of chamber element on the flange element outward from the mid-point of the flange element effectively increases the vacuum cross section and therefore effective contact pressure of the therapy device at that point when a therapeutic level of negative pressure is applied. Movement of the edge of the chamber inward has an opposing effect, providing a larger portion of the flange exposed outside the root location and therapy area decreasing the vacuum cross section. In embodiments of the invention the root location of the chamber element on the flange element is approximately demonstrated in the table in FIG. 9. In regions where higher contact pressure is needed, for example where the device approaches the ear of the user, the chamber location can be biased on the flange toward the outer edge increasing the vacuum cross section and effective contact pressure at that point.

In certain embodiments, the chamber element may contain features that further aid in the prevention of regional collapse, bottoming, and transfer of force from one region to another of the therapy device. Absent local points of flexibility, a rigid chamber may experience situations where external pressure could cause a point of high contact pressure for example upon application of a force, by rolling on to a pillow etc., on the device causing a bottoming event or further a rigid chamber may experience situations where external pressure on the device on one side causes a transfer of force to the opposite side of the device. Events such as these may cause discomfort, dislodging of the device or both.

The term "balance" as used herein refers to the contact pressure of the therapy device being approximately equal at each station of the contact surface. This contact pressure is proportional to therapy vacuum levels relative to the contact area of the therapy device. For example, in a comparison, a larger contact area vis. a smaller contact area, under the same therapy vacuum level will provide for lower contact pressure of the therapy device respectively. In an embodiment of the invention, the contact area of the flange relative to the therapy area provides for a contact pressure that may range from approximately 0.9 to approximately 1.5 times the vacuum level and in a preferred embodiment the contact pressure of the flange element is approximately 1.2 times greater than therapy vacuum levels.

The chamber is operably connected to an air pump to produce the therapeutic level of negative pressure within the chamber element. The air pump can be of any type suitable to produce the therapeutic level of negative pressure, for example positive displacement pumps, impulse pumps, velocity pumps, etc. which can include manual squeeze bulbs, rotary pumps, lobe pumps, oscillatory pumps etc. In certain embodiments, the air pump comprises a piezoelectric material configured to provide an oscillatory pumping action wherein the oscillatory pumping motion operates at a frequency greater that 500 Hz.

The air pump may be a separate component connected to the chamber via a hose or tube, or may be configured integrally to the chamber. The air pump can be connected to the chamber element in any suitable fashion, for example an air pump may be externally located outside of the chamber element and connected via a hose or tube, eg. a stationary bed-side pump, or the pump may be integral to chamber, be battery powered, and wearable by the patient. In certain wearable aspects, the air pump is configured to be integral to the chamber. For example, the air pump may be configured to insert into a sealable aperture on the chamber, the air pump tightly fitting through the aperture creating a seal. As used herein a sealable aperture is an opening through an element of the apparatus that can be closed or sealed from one side or the other with another element of the apparatus creating an air-tight or water tight seal.

In a preferred embodiment, a seal is created via surfaces designed to receive an O-ring. As used herein an O-ring is a gasket in the form of a compliant sealing ring made of a pliable material designed to be compressed during assembly creating a seal at the interface. In certain aspects, a complaint sealing ring feature may be an integral, unitary or discrete part of the air pump, the chamber element or both. In certain embodiments, the compliant sealing ring is provided as a component of the air pump. In a preferred embodiment, the compliant sealing ring feature is a molded feature on the inner circumference of the aperture of the chamber element.

In certain aspects of the invention, one or more tangs, tabs and or recesses are present on the chamber element, flange element and or air pump element of the therapy device, which provide one or more guidance feature(s) to ensure a proper orientation of, or mating between one or more device elements. The tangs, tabs and or recesses can be utilized as part of a sensor system to determine various parameters related to use of the therapy device. These parameters can include, but are not limited to, compatibility of the particular air pump element with the therapy device element (e.g., acting as a recognition feature) and correct placement of the air pump element into the aperture of the chamber element. For example, one or more of these tangs, tabs or recesses can be located on the central structural element as a guidance feature for the air pump element such that a recess on the air pump element or chamber element accepts the tang or tab element on the chamber element or air pump element only when the air pump element is inserted through the sealable aperture in the correct orientation. In some applications, a bayonet fitting may be used. This list is not meant to be limiting.

In certain embodiments, together or with one or more of the foregoing, a material, which will act as an adhesive layer between the flange element of the therapy device and the user, is applied to the outer contact surface of the flange element. The purpose of the adhesive layer is to provide a sealing, cushioning and/or sheer absorbing (i.e. abrasion resistant) element to the flange element. As used herein sheer refers to sheer strain which is a deformation of a material in which parallel surfaces can slide past one another, for example the contact surface of the flange element and the skin of the user.

The adhesive layer further must preferentially adhere to the outer contact surface of the negative pressure therapy device and provide a sufficient level of "tack" such that a releasable mechanical anchoring of the therapy device to the skin of the user is achieved. Tack, as used herein, refers to a material property at the interface created between the adhesive layer and the device, and the skin of the user at the other interface created between the user and the device.

The adhesive layer may be applied to the contact surface area of the negative pressure therapy device in any suitable method including but not limited to spraying, painting, placing, etc., in single or multiple layers to achieve the desired cushioning and sealing properties including but not limited to thickness, hardness and tack for example. In additional embodiments, the adhesive layer may be single layer of a uniform thickness or a single layer of a non-uniform thickness covering the contact surface of the negative pressure therapy device. In further embodiments, the adhesive layer may contain a series of parallel adhesive beads spanning the circumference of the contact surface of the negative pressure therapy device wherein the beads can be of a uniform or non-uniform thickness and of a like or varying adhesive and or gel-like material to achieve the desired cushioning and sealing properties.

In certain embodiments, the adhesive layer is present on the contact surface of the negative pressure therapy device at a thickness falling within a range of approximately 0.005-0.060 inches. In certain embodiments, the adhesive layer is present on the contact surface of the negative pressure therapy device at a thickness falling within a range of approximately 0.010-0.050 inches. In further embodiments, the adhesive layer is present on the contact surface of the negative pressure therapy device at a thickness falling within a range of approximately 0.020-0.040 inches.

The adhesive layer may be achieved by using various materials, such as, but not limited to gel, elastomer, viscous solutions, foams and materials of the like. These materials can be of any chemical composition which provides the necessary end use properties (i.e. tack, firmness, medical clearance, etc.). These materials include, but are not limited to polyurethanes, silicones, acrylonitrile butadiene styrene (ABS), hydrogels, and the like. In preferred embodiments, the adhesive layer should have a hardness as measured by ASTM-D2240-00 (American Society for Testing Materials) of between 0 and 50, more preferable between 5 and 30 most preferable between 5 and 15. In certain embodiments the adhesive layer is made of a silicone gel material. The silicone can be any organosilicone which yields the desired properties although polydimethylsiloxane (PDMS) is often chosen.

The adhesive layer may be applied directly to the outer contact surface of the flange element to a desired thickness or in combination with one or more primer layer and or one or more primer layers in combination with one or more adhesion or binding promotor layers to create a lamination stack of materials to a desired thickness. As used herein a "primer" is a substance used as a preparatory coating, acting as a joining surface between the contact surface of the negative pressure therapy device and adhesive layer or an adhesion promoting layer and the adhesive layer. Further, an adhesion promoting layer is a substance used as a coating to preferentially adhere the adhesive layer to the contact surface of the negative pressure therapy device and or the primer layer that is applied to the outer surface of the negative pressure therapy device.

By way of example, a primer layer may be applied to the contact surface of the negative pressure therapy device to a thickness of about 0.005 inches, followed by an adhesive promoting layer to a thickness of approximately 0.005 inches, followed by the application of an adhesive layer to a thickness of approximately 0.040 inches achieving a final thickness of approximately 0.050 inches. A primer layer may be applied directly to the outer contact surface of the negative pressure therapy device followed by the application of the adhesive layer directly to the primer to a desired thickness of approximately 0.050 inches. In additional embodiments, an adhesive promoter may be applied to the contact surface of the negative pressure therapy device followed by the application of the adhesive layer to a desired thickness of approximately 0.050 inches.

In certain embodiments, the adhesive layer is a gel layer. As used herein a gel layer is a layer of material that can have properties that are mostly liquid however behave like solids due to the cross-linked nature of its structure. The material chosen for the gel layer may be of a certain cohesive pliable consistency so as to mold to and conform to complex shapes for example imperfections in the skin. As used herein cohesive pliable consistency, elasticity or firmness of the gel layer is defined as the gel layer's ability to flow, mold and stretch and substantially return its original shape when not applied to a surface. The material chosen for the gel layer may also be of a certain tack so as to mechanically secure to the contact area. As used herein tack is defined as the gel's "stickiness" and is the property that allows the immediate formation of a bond on contact with another surface The adhesive layer material must adhere sufficiently to the therapeutic device such that it stays adhered to the device when the device is removed from the user's skin. Additionally, must have a tack level that is chosen for appropriate performance at the user's skin interface. That is, at too great a level of tack removal of the device from the skin can be difficult, painful or injurious. While insufficient tack can allow the device to move during use or allow the seal to the skin to open thereby losing the vacuum. The level of tack can be measured by a texture analyzer. For example, using a TA.XT plus with a 7 mm radius and 1 inch diameter spherical head the peak adhesion values should be in a range of 200 to 400 grams peak force more preferably 250 to 350 grams peak force and most preferably 275-325 grams peak force.

As discussed above the tack of the adhesive layer is optimized to achieve a releasable but mechanical anchor of the therapy device to the patient. In certain embodiments, the contact surface of the flange element is coated with a primer to preferentially anchor the adhesive layer to the negative pressure therapy device over the contact region of the user.

In certain embodiments, the adhesive layer is formed from a washable silicone gel such that when washed and allowed to dry, the adhesive layer returns towards an initial tack. In certain embodiments, the silicone gel is chosen from a group with properties that can be controlled including, but not limited to: cross sectional thickness, degree of cross-linking (and thereby firmness and tack) and viscosity (so as to be processable under desired conditions. As used herein viscosity is measured in cps referring to centipoise (cps) were 1 cps=0.01 g/cm/s.

In an embodiment of the invention the gel layer is prepared from a two-part platinum cured organosilicone mixture with properties equivalent to a silicone gel base having an uncatalyzed viscosity of about 20,000 cps and a crosslinker having an uncatalyzed viscosity of about 300 cps. The final firmness (cps) of the cured gel may be increased by increasing the proportion of the crosslinker in the mixture or decreased by lowering the proportion of the crosslinker in the mix. The tack of the material can be increased by decreasing the proportion of crosslinker in the mixture or decreased by increasing the proportion of crosslinker in the mix. In order to achieve the desired properties using a silicone gel base of 20,000 cps and a crosslinker of 300 cps, the ratio of silicone gel base to crosslinker may range (in parts by weight) from about 10.0:0.01 to about 10.00:10.20

In embodiments of the invention the ratio of 20,000 cps silicone gel base to 300 cps cross linker may further range from about 10.0:0.01 to about 10.0:0.5. In other embodiments of the invention the ratio of 20,000 cps silicone gel base to 300 cps crosslinker may range from about 10.0:0.01 to about 10:0.1. And in further embodiments of the invention the ratio of 20,000 cps silicone gel base to 300 cps crosslinker may range from about 10.0:0.06 to about 10:0.20

By example of the invention the silicone gel base and the crosslinker are mixed in desired ratios and placed under vacuum in order to remove any bubbles in the mixed solution (de-gassing). Following de-gassing, the silicone gel solution is applied to the contact surface of the flange element and allowed to cure. The mixture can achieve full cure in approximately 24 hours at room temperature however in some embodiments a full cure of the silicone gel may be achieved in about 5 minutes by placing the therapy device containing the silicone gel layer at about 150° C. The cure temperature may be adjusted to suit limiting elements of the therapy device, for example lower melting points of other therapy device elements.

In certain embodiments, the adhesive layer is made of a hydrogel. Hydrogels are a three-dimensional network of crosslinked hydrophilic polymer chains that can be crosslinked either physically or chemically. Due to the hydrogel material's significant water content, hydrogels can resemble natural soft tissue more than any other type of polymeric biomaterial. In further embodiments, the hydrogel layer may be found as a hydrocolloid wherein the colloid particles are hydrophilic polymers dispersed in water.

In certain embodiments, the adhesive layer is made of a combination of materials applied side-by side on the outer contact surface of the fluidly sealed chamber. By way of example, a hydrogel material may be applied to the circumference of the center portion of the outer contact surface of the fluidly sealed chamber and a silicone gel material may be applied on either side peripheral to the hydrogel material. In further embodiments where a combination of materials are applied side-by-side on the outer contact surface of the flange element, a silicone gel layer may be applied to the circumference of the center portion of the outer contact surface of the fluidly sealed chamber and a hydrogel material may be applied to either side peripheral to the silicone gel material followed by a final application of a silicone gel material peripheral to the hydrogel material.

As used herein, "user compliance" refers to the patient's adherence to the prescribed usage of a therapy device for example the usage of a device throughout a sleep cycle.

As used herein, "device compliance" refers to the ability of the device or elements of the device to accommodate variation, for example, bending, twisting, compressing and or expanding of the device in response to device application and usage including anatomical variations of the patient.

Aspects of the device may be made of a generally rigid material. The term "generally rigid" as used herein refers to a material which is sufficiently rigid to maintain the integrity of the particular element in question. The skilled artisan will understand that a number of polymers may be used including thermoplastics, some thermosets, and elastomers. Thermoplastic materials become flowing liquids when heated and solids when cooled, they are often capable of undergoing multiple heating/cooling cycles without losing mechanical properties. Thermoset materials are made of prepolymers which upon reaction cure irreversibly into a solid polymer network. Elastomers are viscoelastic materials which exhibit both elastic and viscous properties and can be either a thermoplastic or thermoset. Common thermoplastics include PMMA, cyclic olefin copolymer, ethylene vinyl acetate, polyacrylate, polyaryletherketone, polybutadiene, polycarbonate, polyester, polyetherimide, polysulfone, nylon, polyethylene, and polystyrene. Common thermosets include polyesters, polyurethanes, duroplast, epoxy resins, and polyimides. This list is not meant to be limiting. Functional filler materials such as talc and carbon fibers can be included for purposes of improving stiffness, working temperatures, and part shrinkage.

Aspects of the device may be formed using a number of methods known to those of skill in the art, including but not limited to injection molding, machining, etching, 3D printing, etc. In preferred embodiments, the test device base is injection molded, a process for forming thermoplastic and thermoset materials into molded products of intricate shapes, at high production rates and with good dimensional accuracy. The process typically involves the injection, under high pressure, of a metered quantity of heated and plasticized material into a relatively cool mold—in which the plastic material solidifies. Resin pellets are fed through a heated screw and barrel under high pressure. The liquefied material moves through a runner system and into the mold. The cavity of the mold determines the external shape of the product while the core shapes the interior. When the material enters the chilled cavities, it starts to re-plasticize and return to a solid state and the configuration of the finished part. The machine then ejects the finished parts or products.

Those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The therapy device of the present invention comprises structural member(s) that interfaces outside a targeted therapy area of a patient. In a preferred embodiment, the therapy area is that of the upper airway. The therapy device contains a flexible membrane 100, a flange element 110 and an endoskeleton structure 120 that is used to create a vacuum between an inner surface of the appliance and the skin of the upper neck/chin region. The flexible membrane 100 is secured to a flange element 110 at a single point along the back of the flange that evenly distributes the force across all of the flange element. The flexible membrane 100 may contain one or more arcuate ribs 170 to assist in supporting the flexible membrane and further assist in evenly distributing force across all of the flange element.

The endoskeleton structure 120 may be formed as a discrete element and inserted into the therapy device to assist in supporting the flexible membrane 100 and further assist in evenly distributing force across all of the flange element 110 when a therapeutic level of negative pressure is applied. The endoskeleton structure containing a central support structure 125 with hinge points 130, 135, 140 and 140 for spar members 155, 165 containing a plurality of arcuate spars 160. The central support structure further containing adjustable members 175 used to limit the rotation of the spar member(s) 155, 165.

The flexible membrane 100 and endoskeleton structure may also have a central aperture 105 for the insertion of an air pump and a compliant sealing ring-like feature 121. The device may also use a spacing element 123 between the flexible membrane 100 and the air pump. The device may be formed, molded, or fabricated from any suitable material or combination of materials. Non-limiting examples of such materials suitable for constructing the therapy appliance include plastics, metals, natural fabrics, synthetic fabrics, and the like. The device may also be constructed from a material having resilient memory such as, but not limited to, thermoplastic elastomers (TPEs), silicone, rubber, or urethane. Examples of TPE products include block copolymers such as Thermolast, Hipex, Copec, For Tec E, Santoprene, Termoton, Amitel, Solprene, Engage, Hytrel, Dryflex, Mediprene, Kraton, and Pibiflex; elasomeric alloys such as Thermolast A, Thermolast V, Hipex, Forprene, Termoton-V and Vegaprene; styrenic block copolymers such as Thermolast K, Thermolast M, Sofprene, and Laprene; thermoplastic polyurethanes such as Copec; and thermoplastic olefins such as For-Tec E. This list is not meant to be limiting.

Figure 3:
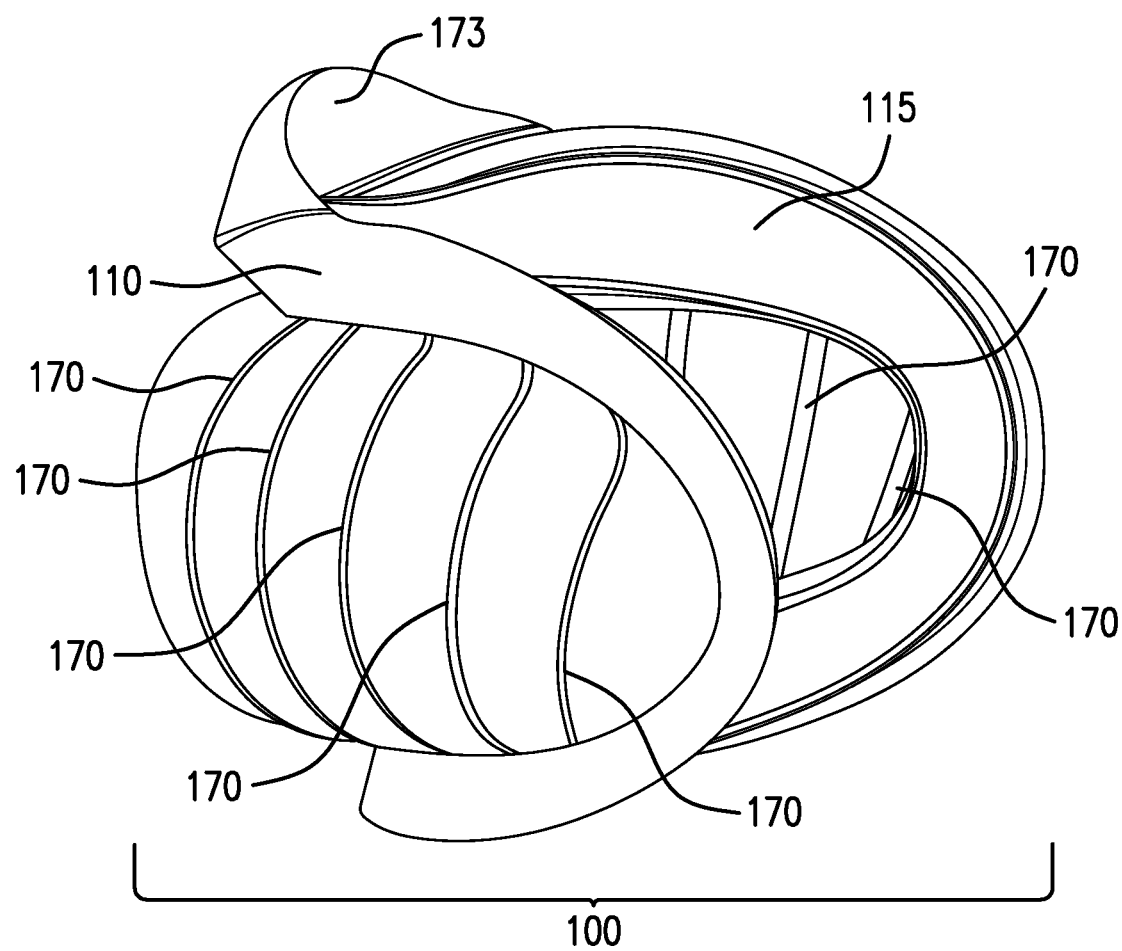
FIG. 3 is a view of an illustrative embodiment of the pressure chamber structure 100, including the sealing element 110, the first surface of the sealing element 115, the chin cup of the sealing element 173, and the plurality of arcuate ribs 170.

In an embodiment of the invention, as can be seen in FIG. 3 showing an expanded view off the endoskeleton structure, the structure contains a central aperture 105, spar member(s) 155 and 154, hinge point(s) 130, 140 and 145, strapping member(s) 105 and 153 and adjustable member(s) 175.

Figure 4:
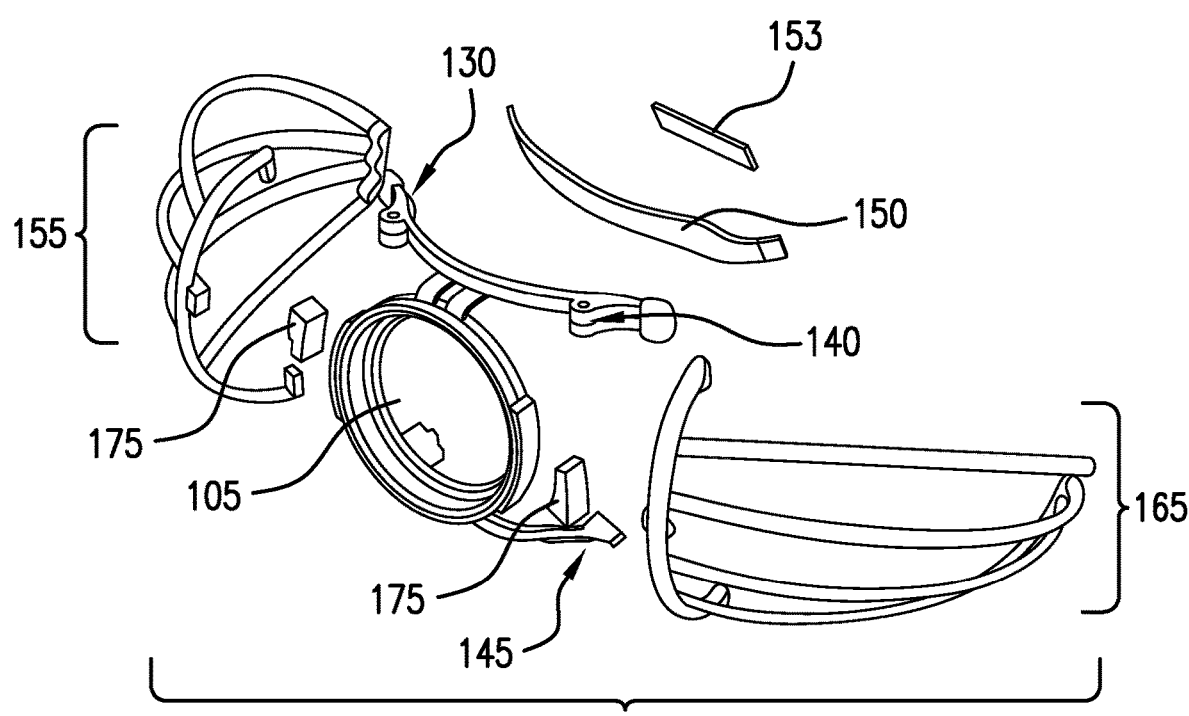
FIG. 4 is a view of an illustrative embodiment of the endoskeleton structure 120 including the central aperture 105, a first hinge point, 130, a third hinge point, 140, a fourth hinge point 145, a first spar member 155, arcuate spar(s) 160, a second spar member 165 and strapping member(s) 150 and 153.
Figure 5:
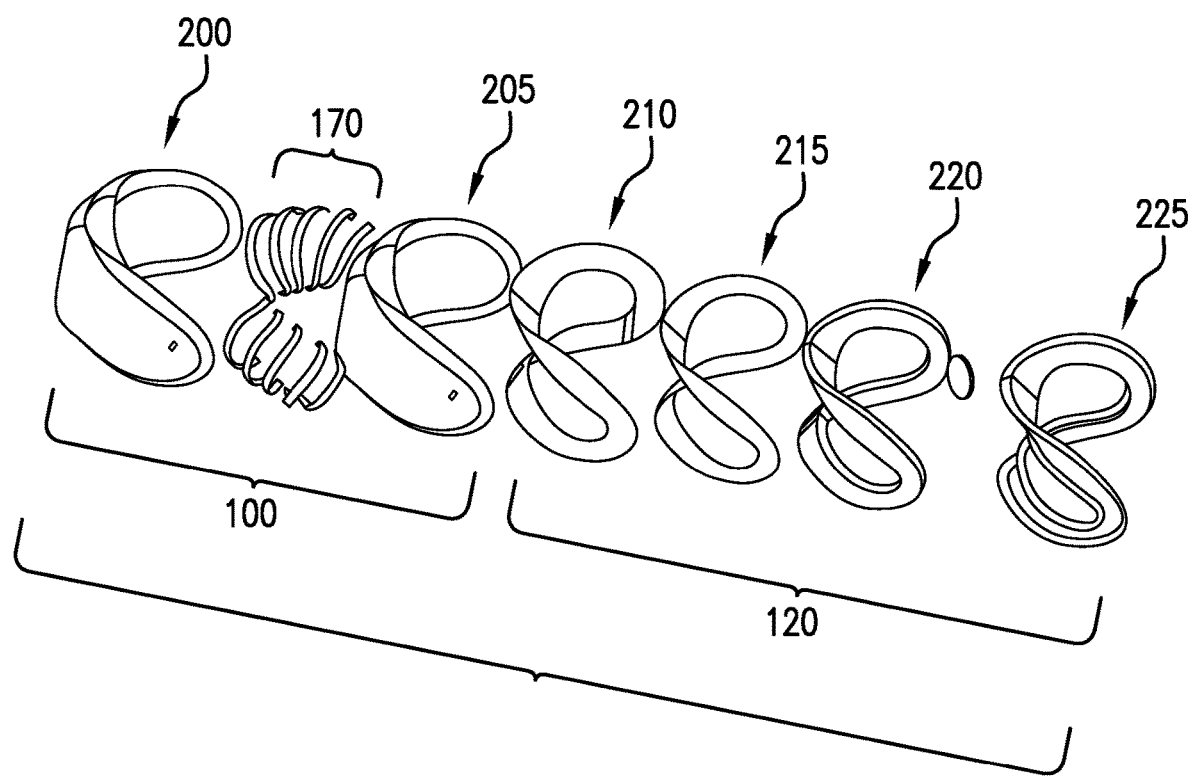
FIG. 5 is a view of an illustrative embodiment of the layers of the pressure containment structure 100, including an outer flexible membrane layer of the pressure containment structure 200, plurality of arcuate ribs 170, an inner flexible membrane layer of the pressure containment structure 205, an inner layer of the sealing element 201, a ribbon element 215, a foam element 220, an outer layer of the sealing element 225, vent element through the outer flexible membrane layer 230 and vent element through the inner flexible membrane layer 235.

In an embodiment of the invention as can be seen in FIG. 4, showing an expanded view of the flexible membrane, the flexible membrane may be made of several layers making up the flexible membrane 100 and flange element 120. The flexible membrane comprising an outer urethane membrane 200 and an inner urethane membrane 205 with a plurality of arcuate ribs located and secured in between the outer 200 and inner 205 flexible membranes. An inner flange membrane 201, a ribbon layer 201, a cushioning layer 220 and outer flange membrane 225

Figure 7:
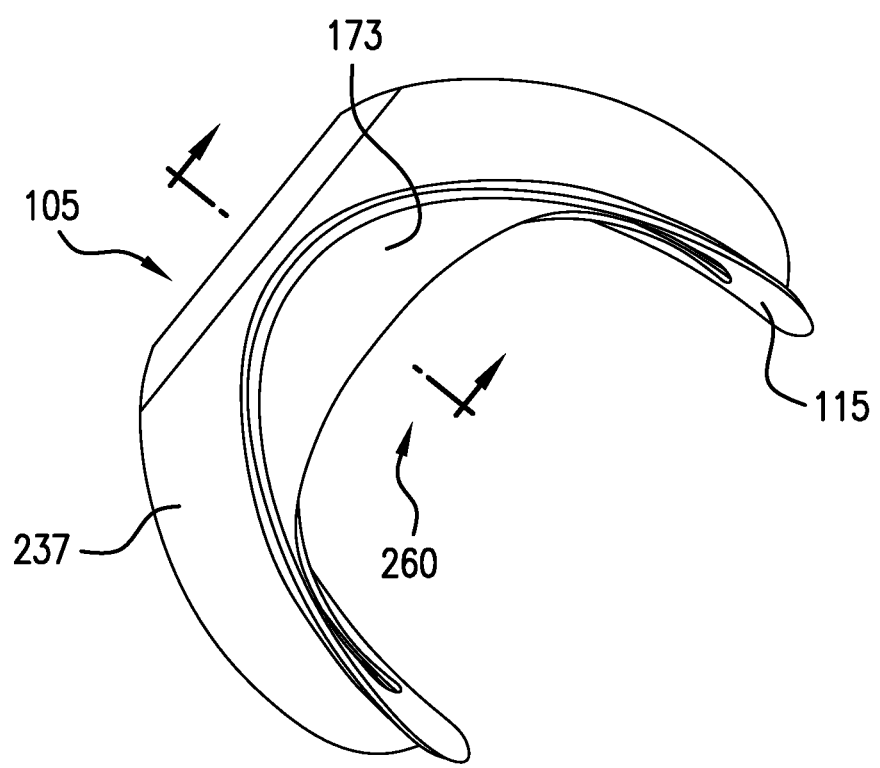
FIG. 7 is a top view of an illustrative embodiment of the therapy device including a central aperture 105, chin cup 173, first surface of the sealing element 115, exterior surface of the flexible membrane 237 and a line bisecting the device 260 including arrows indicating the orientation of the therapy device for the purpose of FIG. 8.
Figure 8:
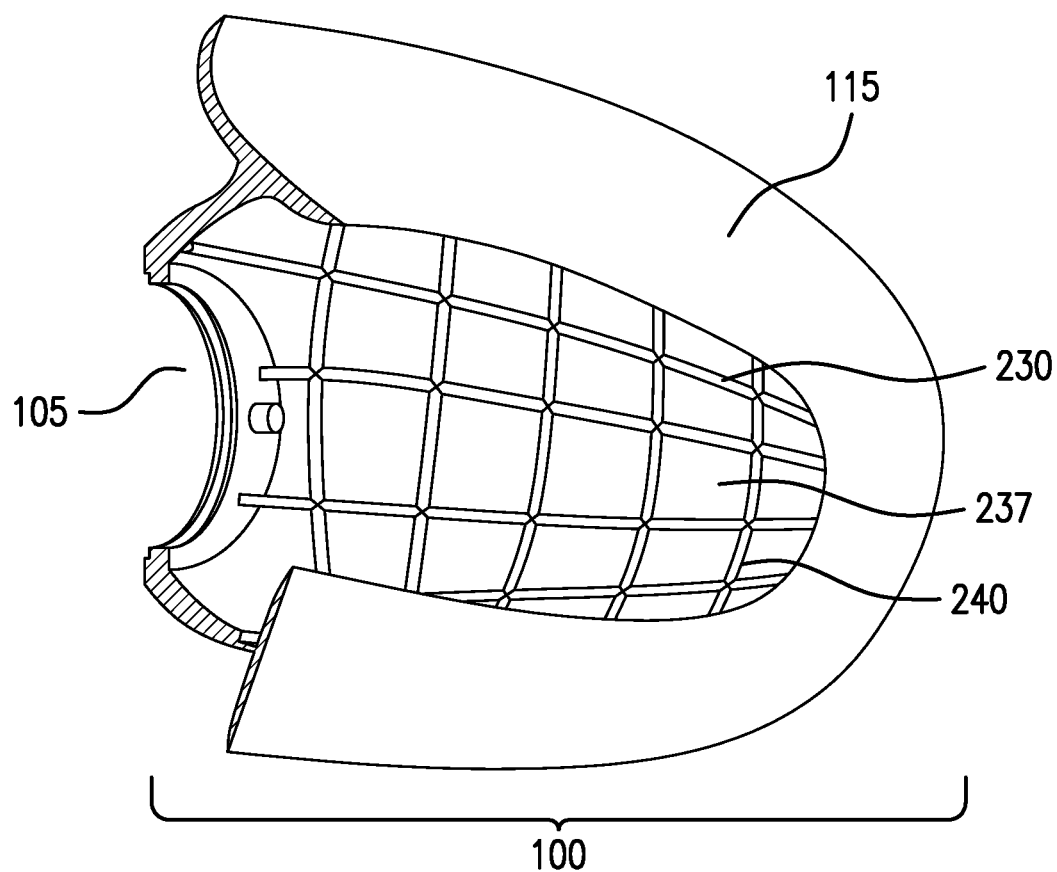
FIG. 8 is a bisected rear view of an illustrative embodiment of the therapy device looking in to the pressure containment structure 100 showing the first surface of the sealing element 115, flexible membrane 237, with a unitary curvilinear support structure comprising vertical curvilinear structural members 240 and horizontal curvilinear structural members 230.

The therapy device of the present invention may also contain structural elements that are unitary to the flexible membrane as seen in FIG. 8. FIG. 7 showing a top view of the therapy device with a bisecting line 260 for the purpose of FIG. 8, with the chin cup 173, central aperture 105, first surface of the sealing element 115, and exterior of the flexible membrane. FIG. 8 shows a bisected view of an embodiment of the pressure containment structure 100, containing a central aperture 105, first surface of the sealing element 115 including structural elements molded into the flexible membrane 237 where there are horizontal curvilinear structural members 230 and vertical curvilinear structural members 240 to assist in the support of the flexible membrane and distribution of load across the first surface of the sealing surface 115 when a therapeutic level of negative pressure is applied.

Figure 9A:
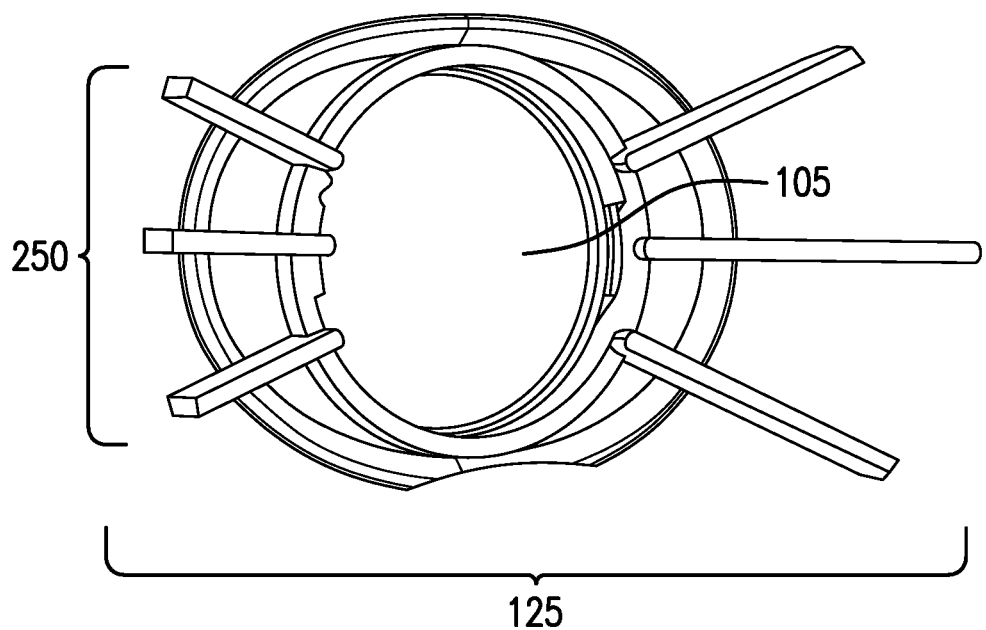
FIG. 9a is a rear view of an illustrative embodiment of a discrete central support structure 125 including the central aperture 105 and a plurality of supporting structures 250
Figure 9B:
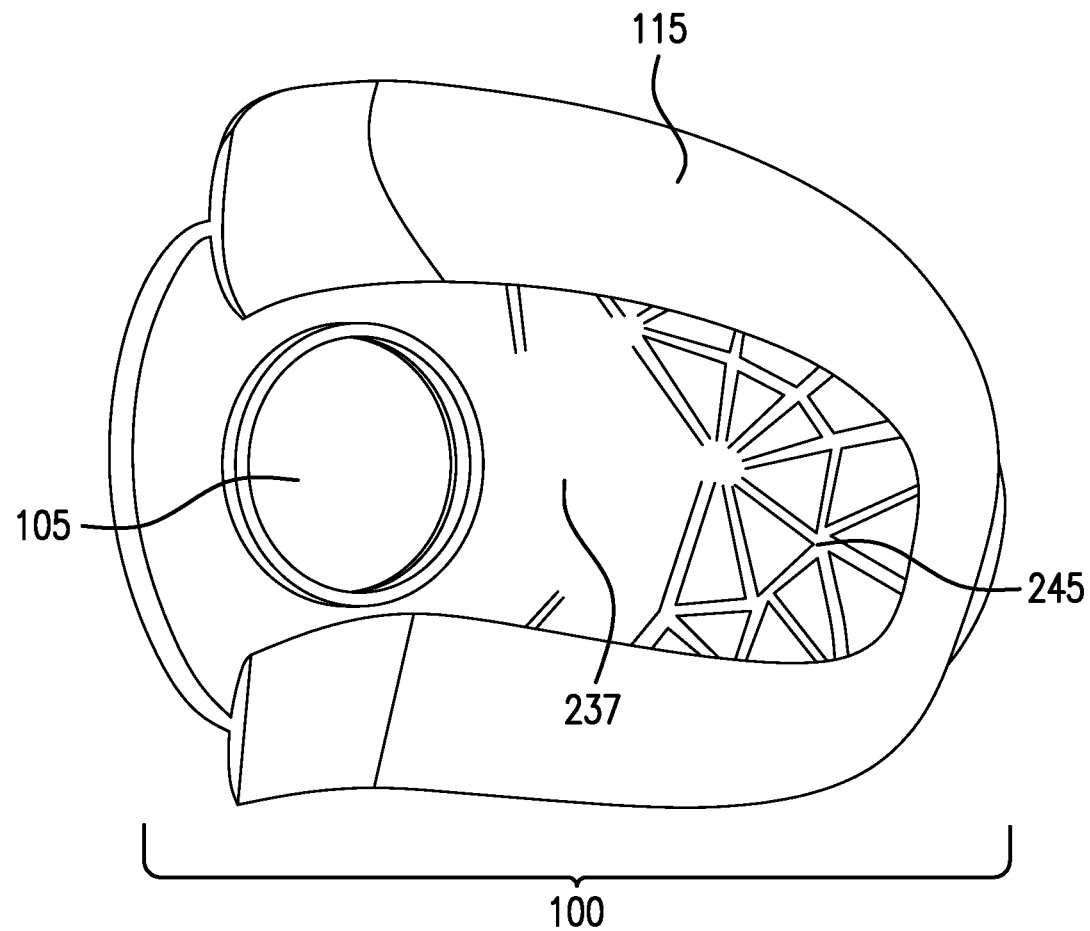
FIG. 9b is a partial rear view of an illustrative embodiment of the pressure containment structure 100, including the first surface of the sealing element 115, flexible membrane 237, with curvilinear support structure 245.
Figure 9C:
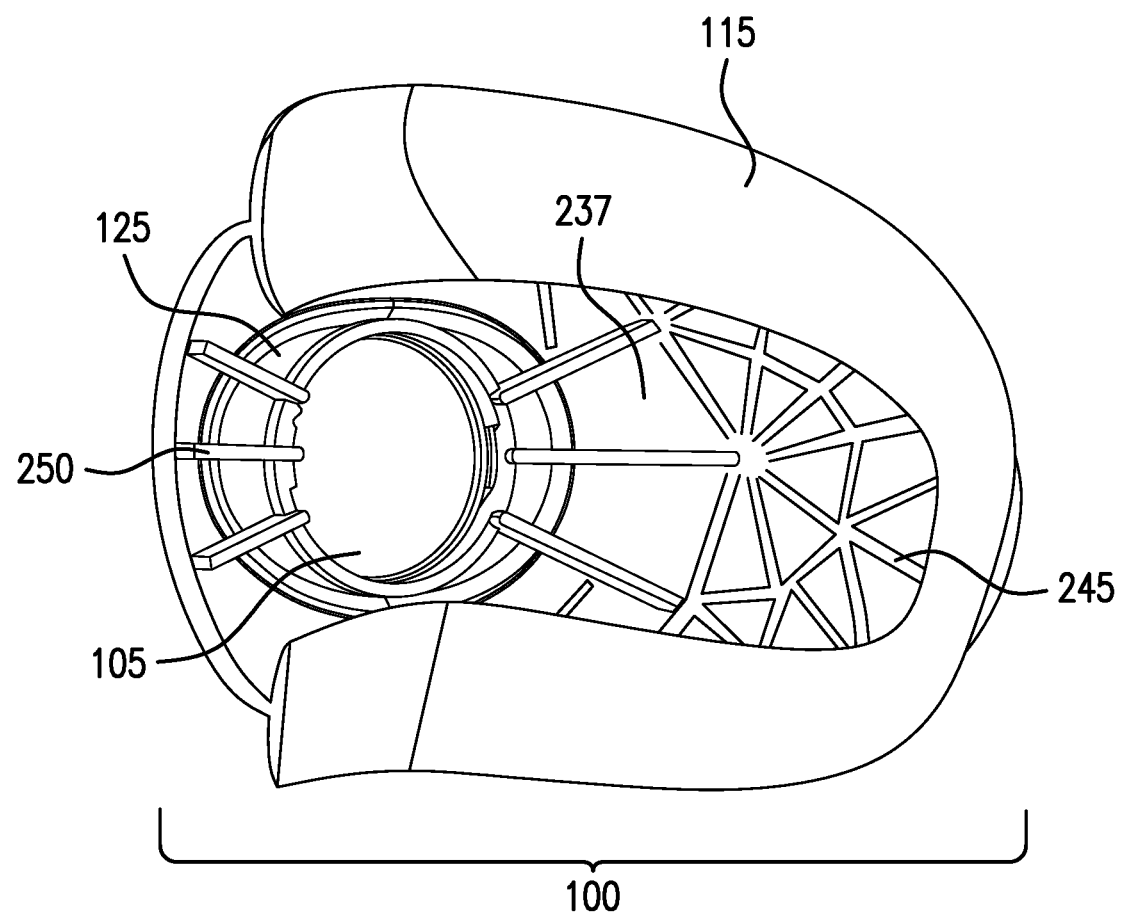
FIG. 9c is a partial rear view of an illustrative embodiment of the pressure containment structure 100 with the central support structure 125 including a plurality of supporting structures installed in to the pressure containment structure 100, including a central aperture 105, the first surface of the sealing element 115, flexible membrane 237, and unitary curvilinear support structure 245.

The therapy device of the present invention may also contain structural elements that are both discrete and unitary to the pressure containment structure. For example, FIG. 9a shows a discrete central structural member containing a central aperture and a plurality of supporting structures 250 and FIG. 9b, shows a partial rear view of the pressure containment structure 100, containing a central aperture 105, first surface of the sealing element 115, flexible membrane and a unitary support matrix 245. Upon assembly, FIG. 9c, the central structural member 125 with its plurality of supporting structures 250 and the unitary support matrix 245 of the flexible membrane 237 complete the supporting elements of the pressure containment structure 100. The supporting elements assisting in the support of the flexible membrane and distribution of load across the sealing surface 115 when a therapeutic level of negative pressure is applied.

Figure 10:
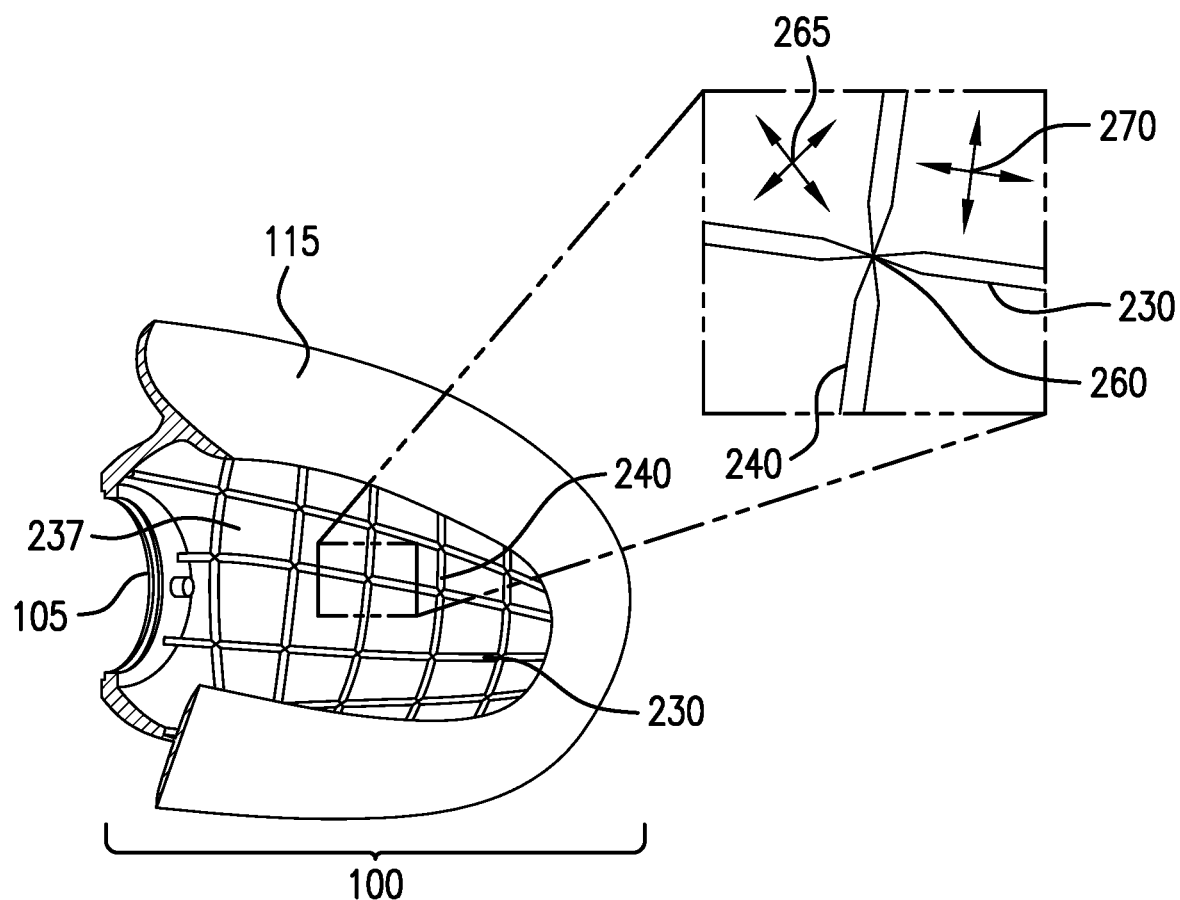
FIG. 10 is a bisected rear view of an illustrative embodiment of the therapy device looking in to the pressure containment structure 100 showing the first surface of the sealing element 115, flexible membrane 237, with a unitary curvilinear support structure 245 comprising vertical curvilinear structural members 240, horizontal curvilinear structural members 230 and detail box showing a closer view of a point of intersection of the horizontal curvilinear structural members 230 and vertical curvilinear structural members 240 where the tapering of the curvilinear structural members at their point of intersection creates a living hinge 260. Also shown are arrows that indicate the direction of force vectors 270 and approximate direction of sheer 265.

Elements that are unitary to the flexible membrane as seen in FIG. 10, showing a bisected view of an embodiment of the pressure containment structure 100, containing a central aperture 105, first surface of the sealing element 115 including structural elements molded into the flexible membrane 237 where there are horizontal curvilinear structural members 230 and vertical curvilinear structural members 240 can be designed to assist in the support of the flexible membrane can impart sectional properties and directional properties. As seen in FIG. 8 and FIG. 10, at the intersection of vertical curvilinear structural members 240 and horizontal curvilinear structural members, the intersection may contain features like tapering of width and thickness of integrated features to create a living hinge 260. Wherein the living hinge allows sheer movement of the flexible membrane 265 in one or many directions as well as structural properties in one or many directions as shown with the arrows indicating the direction of force vectors 270. Sheer movement provides flexibility of the pressure containment suction 100 while directional properties provide for distribution of load across the sealing surface 115 when a therapeutic level of negative pressure is applied.

Device balancing may also be accomplished through variation in other structural elements of the chamber or flange both locally and throughout the contact surface, for example length or width of the flexible membrane, flange thickness, endoskeleton structure shape and features and shape of the central bend of the device alone, whole or in part. In a preferred embodiment, the structural elements including the aspect ratio of the flange may change to provide minimal variation in contact pressure wherein the contact pressure is approximately 1.2 times that of the applied vacuum at all contact points of the flange element.

Structural embodiments of the apparatus may vary based on the size of the device and the description provided herein is a guide to the functional aspects and means.

The following are exemplary embodiments of the invention:

1. A therapy device configured for the administration of negative pressure upon the external surface of the individual, the therapy device comprising: a chamber comprising
   a. a pressure containment structure comprising
      (i) a flexible membrane which defines a chamber,
      (ii) an aperture through the flexible membrane, and
      (iii) a flange element adapted to form a sealing surface when mated to the individual, wherein a first surface of the flange element is configured to approximately conform to a continuous contact area on the individual defined by a first location corresponding to a first gonion on one side of the individual's mandibular body, a second location corresponding to the individual's mental protuberance, a third location corresponding to a second gonion on the opposite side of the individual's mandibular body, and a fourth location corresponding to the individual's thyroid cartilage,
   b. a skeleton structure that is formed as a discrete element from the pressure containment structure, the skeleton structure configured to be positioned inside the pressure containment structure and comprising
      (i) a structural member configured to mechanically support the aperture and comprising first and second hinge points on a first side thereof and third and fourth hinge points on a second side thereof,
      (ii) a strapping member that extends at least from the first hinge point to the third hinge point and is configured to contact the flange element at a location within the chamber which corresponds to the second location,
      (iii) a first spar member configured to mechanically support the chamber and comprising a plurality of arcuate spars, wherein each spar in the first spar member is configured to extend from a first end thereof that is located proximal to the structural member to a second end thereof that is located at the flange element at the first location, wherein each of the spars in the first spar member are spaced apart laterally from one another, wherein each of the spars in the first spar member are affixed to a first lateral joining structure at the first end thereof and to a second lateral joining structure at the second end thereof, and wherein the first lateral joining structure is rotationally engaged with the structural member at the first and second hinge points thereof,
      (iv) a second spar member configured to mechanically support the chamber and comprising a plurality of arcuate spars, wherein each spar in the second spar member is configured to extend from a first end thereof that is located proximal to the structural member to a second end thereof that is located at the flange element at the third location, wherein each of the spars in the second spar member are spaced apart laterally from one another, wherein each of the spars in the second spar member are affixed to a third lateral joining structure at the first end thereof and to a fourth lateral joining structure at the second end thereof, and wherein the third lateral joining structure is rotationally engaged with the structural member at the third and fourth hinge points thereof,
      (iv). a first plurality of arcuate ribs running approximately perpendicular to the spars of the first spar member, wherein each rib in the first plurality of ribs are spaced apart laterally from one another and physically constrained to maintain an inter-rib spacing, wherein each rib in the first plurality of ribs is configured to extend from a first end thereof that is located at the flange element as it extends from the first location to the second location to a second end thereof that is located at the flange element as it extends from the first location to the fourth location, and
      (v). a second plurality of arcuate ribs running approximately perpendicular to the spars of the second spar member, wherein each rib in the second plurality of ribs are spaced apart laterally from one another and physically constrained to maintain an inter-rib spacing, wherein each rib in the second plurality of ribs is configured to extend from a first end thereof that is located at the flange element as it extends from the third location to the second location to a second end thereof that is located at the flange element as it extends from the second location to the fourth location; and
   (c) an air pump operably connected to the chamber at the aperture to produce the therapeutic level of negative pressure within the chamber.

2. A therapy device according to embodiment 1, wherein the first and third hinge points are configured to be positioned on opposite sides of the mental protuberance and the second and fourth hinge points are configured to be positioned on opposite sides of the thyroid cartilage when the chamber is mated to the individual.

3. A therapy device according to embodiment 1 or 2, wherein the inter-rib spacing of the first and second plurality of ribs is maintained by affixing each rib to the flexible membrane.

4. A therapy device according to one of embodiments 1-3, wherein the inter-rib spacing of the first and second plurality of ribs is maintained by affixing each rib to one or more of the spars.

5. A therapy device according to one of embodiments 1-4, wherein the inter-rib spacing of the first and second plurality of ribs is maintained by affixing each rib to one or more adjacent rib.

6. A therapy device according to one of embodiments 1-5, wherein each spar in the first and second spar members comprises a first curved surface which is configured to face towards the outer aspect of the flexible membrane and which lies in contact with an inner surface of the chamber.

7. A therapy device according to embodiment 5, wherein the first curved surface is configured to form a parallel curve to the inner surface of the chamber at the points of contact therewith.

8. A therapy device according to embodiment 5 or 6, wherein contact between the first curved surface and the inner surface creates a shear force that resists lateral movement of the first curved surface relative to the inner surface.

9. A therapy device according to one of embodiments 1-8, wherein each rib in the first and second plurality of ribs comprises a first curved surface which is configured to face towards the outer aspect of the flexible membrane.

10. A therapy device according to one of embodiments 1-9, wherein the first and second spar members are configured to distribute load from the region of the chamber proximal to the structural member to the region of the device proximal to the first and second gonion when the chamber is mated to the individual and an effective level of negative pressure is applied within the chamber.

11. A therapy device according to one of embodiments 1-10, wherein one or more, and preferably each, of the first, second, third and fourth hinge points engages with the first and/or second spar members using a living hinge.

12. A therapy device according to one of embodiments 1-11, wherein one or more, and preferably each, of the first, second, third and fourth hinge points engages with the first and/or second spar members using a pivoting joint.

13. The therapy device of one of embodiments 1-12, wherein the air pump is wearable by the patient and is battery powered.

14. The therapy device of one of embodiments 1-13, wherein the air pump is configured integrally to the pressure containment structure.

15. The therapy device of one of embodiments 1-14, wherein the air pump comprises a piezoelectric material configured to provide an oscillatory pumping motion 16. The therapy device of embodiment 15, wherein the oscillatory pumping motion operates at a frequency greater than 500 Hz.

17. The therapy device of one of embodiments 13-16, wherein the air pump engages through the aperture with the structural member and forms an airtight seal with the flexible membrane.

18. A therapy device according to embodiment 17, wherein the air pump engages with the structural member using a bayonet mount.

19. A therapy device of one of embodiments 17 or 18, wherein the aperture comprises a compliant sealing ring onto which the air pump engages.

20. A therapy device according to one of embodiments 1-19, wherein the flexible membrane is molded from a material selected from the group consisting of urethane, silicone, and a thermoplastic elastomer.

21. A therapy device according to one of embodiments 1-20, wherein the structural member comprises a first adjustable member which provides a structure configured to physically limit rotation of the first spar member at the first and second hinge points, and a second adjustable member which provides a structure configured to physically limit rotation of the second spar member at the third and fourth hinge points.

22. A therapy device according to embodiment 21, wherein the first and second adjustable members are configured to provide a predetermined range to an unloaded spacing measured between the first and third locations.

23. A therapy device according to embodiment 22, wherein the unloaded spacing is narrower than a spacing obtained when the chamber is mated to the individual and the therapeutic level of negative pressure is applied within the chamber such that a preload force is applied to the individual by the chamber prior to the application of negative pressure, and wherein the predetermined range is configured to provide a predetermined range to the preload force.

24. The therapy device of one of embodiments 1-23, wherein the flexible membrane comprises one or more vent elements configured to provide an airflow into the chamber of between about 30 mL/min and about 100 mL/min when the chamber is mated to the individual and the therapeutic level of negative pressure is applied within the chamber.

25. The therapy device of embodiment 24, wherein the vent elements are configured to provide an airflow of between about 30 mL/min and about 50 mL/min.

26. The therapy device of embodiment 24 or 25, wherein the vent element comprises an aperture and a filter element within the aperture, wherein the filter element comprises a pore size of about 1.0 μm or less.

27. The therapy device of embodiment 26, wherein the filter element comprises a pore size of about 0.7 μm.

28. The therapy device of one of embodiments 26-27, wherein the filter element is configured as a replaceable element.

29. The therapy device of one of embodiments 24-25, wherein the vent element comprises one or a plurality of holes between about 25 μm and about 200 μm in diameter.

30. The therapy device of one of embodiments 24-29, wherein the vent elements are located distal to the pump element to induce airflow through the chamber, wherein air enters the chamber via the vent elements and is exhausted via the pump element.

31. A method of applying negative pressure therapy to an individual in need thereof, comprising mating a therapy device according to one of embodiments 1-30 to the individual, and applying a therapeutic level of negative pressure within the chamber, thereby increasing patency of the airway of the individual.

32. A method according to embodiment 31, wherein the negative pressure therapy is for treatment of sleep apnea.

33. A method according to embodiment 31, wherein the negative pressure therapy is for treatment of snoring.

34. A method according to embodiment 31, wherein the negative pressure therapy is for treatment of full or partial upper airway collapse.

35. A method according to embodiment 31, wherein the negative pressure therapy is for treatment of full or partial upper airway obstruction.

36. A therapy device configured for the administration of negative pressure upon the external surface of the individual, the therapy device comprising:
 a. a pressure containment structure comprising (i) a flexible membrane which defines a chamber,
(ii) an aperture through the flexible membrane, and
(iii) a flange element adapted to form a sealing surface when mated to the individual, wherein a first surface of the flange element is configured to approximately conform to a continuous contact area on the individual defined by a first location corresponding to a first gonion on one side of the individual's mandibular body, a second location corresponding to the individual's mental protuberance, a third location corresponding to a second gonion on the opposite side of the individual's mandibular body, and a fourth location corresponding to the individual's thyroid cartilage;

b. an curvilinear structure that is formed as unitary elements of the pressure containment structure, the curvilinear structure comprising
(i) a structural member configured to mechanically support the aperture and comprising first spar attachments locations on a first side thereof and second spar attachment locations on a second side thereof,
(ii) a first plurality of spars configured to mechanically support the pressure containment structure, wherein each spar is unitary with the first spar attachment locations at a first end thereof and each spar extends at a second end thereof to the flange element at the first location, wherein each of the spars in the first plurality of spars are spaced apart laterally from one another,
(iii) a second plurality of spars configured to mechanically support the pressure containment structure, wherein each spar is unitary with the second spar attachment locations at a first end thereof and each spar extends at a second end thereof to the flange element at the third location, wherein each of the spars in the second plurality of spars are spaced apart laterally from one another;
(iv) a first plurality of arcuate ribs running approximately perpendicular to the spars of the first plurality of spars, wherein each rib in the first plurality of ribs are spaced apart laterally from one another and intersect with the first plurality of spars in a unitary manner, wherein each rib in the first plurality of ribs is configured to extend from a first end thereof that is located at the flange element as it extends from the first location to the second location to a second end thereof that is located at the flange element as it extends from the first location to the fourth location; and
(v). a second plurality of arcuate ribs running approximately perpendicular to the spars of the second plurality of spars, wherein each rib in the second plurality of ribs are spaced apart laterally from one another and intersect with the second plurality of spars in a unitary manner, wherein each rib in the second plurality of ribs is configured to extend from a first end thereof that is located at the flange element as it extends from the third location to the second location to a second end thereof that is located at the flange element as it extends from the second location to the fourth location; and (c) an air pump operably connected to the chamber at the aperture to produce the therapeutic level of negative pressure within the chamber.

37. A therapy device according to embodiment 36, wherein the spars are configured to distribute load from the region of the chamber proximal to the structural member to the region of the device proximal to the first and second gonion when the chamber is mated to the individual and an effective level of negative pressure is applied within the chamber.

38. The therapy device of one of embodiments 36 and 37, wherein the air pump is wearable by the patient and is battery powered.

39. The therapy device of embodiment 38, wherein the air pump is configured integrally to the pressure containment structure.

40. The therapy device of one of embodiments 36-39 wherein the air pump comprises a piezoelectric material configured to provide an oscillatory pumping motion 41. The therapy device of embodiment 40, wherein the oscillatory pumping motion operates at a frequency greater than 500 Hz.

42. The therapy device of one of embodiments 36-41, wherein the air pump engages through the aperture with the structural member and forms an airtight seal with the flexible membrane.

43. A therapy device according to embodiment 42, wherein the air pump engages with the structural member using a bayonet mount.

44. A therapy device of one of embodiments 42 and 43, wherein the aperture comprises a compliant sealing ring onto which the air pump engages.

45. A therapy device according to one of embodiments 36-44, wherein the flexible membrane is molded from a material selected from the group consisting of urethane, silicone, and a thermoplastic elastomer.

46. A therapy device according to one of embodiments 36-45, wherein the unloaded spacing is narrower than a spacing obtained when the chamber is mated to the individual and the therapeutic level of negative pressure is applied within the chamber such that a preload force is applied to the individual by the chamber prior to the application of negative pressure, and wherein the predetermined range is configured to provide a predetermined range to the preload force.

47. The therapy device of one of embodiments 36-46, wherein the flexible membrane comprises one or more vent elements configured to provide an airflow into the chamber of between about 30 mL/min and about 100 mL/min when the chamber is mated to the individual and the therapeutic level of negative pressure is applied within the chamber.

48. The therapy device of embodiment 47, wherein the vent elements are configured to provide an airflow of between about 30 mL/min and about 50 mL/min.

49. The therapy device of one of embodiments 47-48, wherein the vent element comprises an aperture and a filter element within the aperture, wherein the filter element comprises a pore size of about 1.0 µm or less.

50. The therapy device of embodiment 49, wherein the filter element comprises a pore size of about 0.7 µm.

51. The therapy device of one of embodiments 49-50, wherein the filter element is configured as a replaceable element.

52. The therapy device of one of embodiments 48-49, wherein the vent element comprises one or a plurality of holes between about 25 µm and about 200 µm in diameter.

53. The therapy device of one of embodiments 47-52, wherein the vent elements are located distal to the pump element to induce airflow through the chamber, wherein air enters the chamber via the vent elements and is exhausted via the pump element.

54. A method of applying negative pressure therapy to an individual in need thereof, comprising mating a therapy device according to one of embodiments 36-53 to the individual, and applying a therapeutic level of negative pressure within the chamber, thereby increasing patency of the airway of the individual.

55. A method according to embodiment 54, wherein the negative pressure therapy is for treatment of sleep apnea.

56. A method according to embodiment 54, wherein the negative pressure therapy is for treatment of snoring.

57. A method according to embodiment 54, wherein the negative pressure therapy is for treatment of full or partial upper airway collapse.

58. A method according to embodiment 54 wherein the negative pressure therapy is for treatment of full or partial upper airway obstruction.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims:

What is claimed is:

1. A therapy device configured for the administration of negative pressure upon an external surface of an individual, the therapy device comprising:
a chamber comprising
   (a) a pressure containment structure comprising
      (i) a flexible membrane which defines a chamber,
      (ii) an aperture through the flexible membrane, and
      (iii) a flange element adapted to form a sealing surface when mated to the individual,
      wherein a first surface of the flange element is configured to approximately conform to a continuous contact area on the individual defined by a first location corresponding to a first gonion on one side of the individual's mandibular body, a second location corresponding to the individual's mental protuberance, a third location corresponding to a second gonion on an opposite side of the individual's mandibular body, and a fourth location corresponding to the individual's thyroid cartilage,
   (b) a skeleton structure that is formed as a discrete element from the pressure containment structure, the skeleton structure configured to be positioned inside the pressure containment structure and comprising
      (i) a structural member configured to mechanically support the aperture and comprising a first hinge point and a second hinge point on a first side thereof and a third hinge point and a fourth hinge point on a second side thereof,
      (ii) a strapping member that extends at least from the first hinge point to the third hinge point and is configured to contact the flange element at a location within the chamber which corresponds to the second location,
      (iii) a first spar member configured to mechanically support the chamber and comprising a plurality of arcuate spars, wherein each arcuate spar in the first spar member is configured to extend from a first end thereof located proximal to the structural member to a second end thereof located at the flange element at the first location, wherein each of the arcuate spars in the first spar member are spaced apart laterally from one another, wherein each of the arcuate spars in the first spar member are affixed to a first lateral joining structure at the first end thereof and to a second lateral joining structure at the second end thereof, and wherein the first lateral joining structure is rotationally engaged with the structural member at the first and second hinge points thereof,
      (iv) a second spar member configured to mechanically support the chamber and comprising a plurality of arcuate spars, wherein each arcuate spar in the second spar member is configured to extend from a first end thereof located proximal to the structural member to a second end thereof located at the flange element at the third location, wherein each of the arcuate spars in the second spar member are spaced apart laterally from one another, wherein each of the arcuate spars in the second spar member are affixed to a third lateral joining structure at the first end thereof and to a fourth lateral joining structure at the second end thereof, and wherein the third lateral joining structure is rotationally engaged with the structural member at the third and fourth hinge points thereof,
   (c) a first plurality of arcuate ribs running approximately perpendicular to the arcuate spars of the first spar member, wherein each arcuate rib in the first plurality of ribs are spaced apart laterally from one another and physically constrained to maintain an inter-rib spacing, wherein each arcuate rib in the first plurality of ribs is configured to extend from a first end thereof located at the flange element as said arcuate rib extends from the first location to the second location to a second end thereof located at the flange element as said arcuate rib extends from the first location to the fourth location, and
   (d) a second plurality of arcuate ribs running approximately perpendicular to the arcuate spars of the second spar member, wherein each arcuate rib in the second plurality of ribs are spaced apart laterally from one another and physically constrained to maintain an inter-rib spacing, wherein each arcuate rib in the second plurality of ribs is configured to extend from a first end thereof located at the flange element as said arcuate rib extends from the third location to the second location to a second end thereof located at the flange element as said arcuate rib extends from the second location to the fourth location; and an air pump operably connected to the chamber at the aperture to produce a therapeutic level of negative pressure within the chamber.

2. A therapy device according to claim 1, wherein the first and third hinge points are configured to be positioned on opposite sides of the mental protuberance and the second and fourth hinge points are configured to be positioned on opposite sides of the thyroid cartilage when the chamber is mated to the individual.

3. A therapy device according to claim 1, wherein the inter-rib spacing of the first and second plurality of arcuate ribs is maintained by affixing each arcuate rib of the first and second plurality of arcuate ribs to the flexible membrane.

4. A therapy device according to claim 1, wherein the inter-rib spacing of the first and second plurality of arcuate ribs is maintained by affixing each arcuate rib of the first and second plurality of arcuate ribs to one or more of the arcuate spars of the first and second spar members.

5. A therapy device according to claim 1, wherein the inter-rib spacing of the first and second plurality of arcuate ribs is maintained by affixing each arcuate rib of the first and second plurality of arcuate ribs to one or more adjacent arcuate ribs of the first and second plurality of arcuate ribs.

6. A therapy device according to claim 1, wherein each arcuate spar in the first and second spar members comprises a first curved surface which is configured to face towards an outer aspect of the flexible membrane and which lies in contact with an inner surface of the chamber.

7. A therapy device according to claim 6, wherein the first curved surface is configured to form a parallel curve to the inner surface of the chamber at one or more points of contact therewith.

8. A therapy device according to claim 7, wherein contact between the first curved surface and the inner surface creates a shear force that resists lateral movement of the first curved surface relative to the inner surface.

9. A therapy device according to claim 1 having one or more of the following characteristics:

each arcuate rib in the first and second plurality of arcuate ribs comprises a first curved surface which is configured to face towards an outer aspect of the flexible membrane;

the first and second spar members are configured to distribute load from a region of the chamber proximal to the structural member to a region of the device proximal to the first and second gonion when the chamber is mated to the individual and an effective level of negative pressure is applied within the chamber;

each of the first, second, third and fourth hinge points engages with the first and/or second spar members using a living hinge; and each of the first, second, third and fourth hinge points engages with the first and/or second spar members using a pivoting joint;

the air pump is wearable by the patient and is battery powered and configured integrally to the pressure containment structure;

the air pump comprises a piezoelectric material configured to provide an oscillatory pumping motion, wherein the oscillatory pumping motion operates at a frequency greater than 500 Hz;

the air pump engages through the aperture with the structural member and forms an airtight seal with the flexible membrane, wherein the air pump engages with the structural member using a bayonet mount;

the aperture comprises a compliant sealing ring onto which the air pump engages;

the flexible membrane is molded from a material selected from the group consisting of urethane, silicone, and a thermoplastic elastomer;

the structural member comprises a first adjustable member which provides a structure configured to physically limit rotation of the first spar member at the first and second hinge points, and a second adjustable member which provides a structure configured to physically limit rotation of the second spar member at the third and fourth hinge points;

the first and second adjustable members are configured to provide a predetermined range to an unloaded spacing measured between the first and third locations, wherein the unloaded spacing is narrower than a spacing obtained when the chamber is mated to the individual and the therapeutic level of negative pressure is applied within the chamber such that a preload force is applied to the individual by the chamber prior to application of negative pressure, and wherein the predetermined range is configured to provide a predetermined range to the preload force; and the flexible membrane comprises one or more vent elements configured to provide an airflow into the chamber of between about 30 mL/min and about 100 mL/min when the chamber is mated to the individual and the therapeutic level of negative pressure is applied within the chamber, wherein the one or more vent elements are configured to provide an airflow of between about 30 mL/min and about 50 mL/min and the one or more vent elements further comprise an aperture and a filter within the aperture, wherein the filter comprises a pore size of about 1.0 µm or less.

10. The therapy device of claim 9, wherein the flexible membrane comprises the filter within the aperture.

11. The therapy device of claim 9, wherein the flexible membrane comprises the one or more vent elements, wherein the one or more vent elements comprise one or a plurality of holes between about 25 µm and about 200 µm in diameter.

12. The therapy device of claim 11, wherein the one or more vent elements are located distal to the air pump to induce airflow through the chamber, wherein air enters the chamber via the one or more vent elements and is exhausted via the air pump.

13. A method of applying negative pressure therapy to an individual in need thereof, comprising mating the therapy device according to claim 1 to the individual, and applying the therapeutic level of negative pressure within the chamber, thereby increasing patency of the airway of the individual.

14. A method according to claim 13, wherein the negative pressure therapy is for treatment of sleep apnea.

15. A method according to claim 13, wherein the negative pressure therapy is for treatment of snoring.

16. A method according to claim 13, wherein the negative pressure therapy is for treatment of full or partial upper airway collapse.

17. A method according to claim 13, wherein the negative pressure therapy is for treatment of full or partial upper airway obstruction.

\* \* \* \* \*